(12) United States Patent
Bamdad

(10) Patent No.: US 7,615,340 B2
(45) Date of Patent: Nov. 10, 2009

(54) ELECTRONIC DETECTION OF INTERACTION AND DETECTION OF INTERACTION BASED ON THE INTERRUPTION OF FLOW

(75) Inventor: Cynthia C. Bamdad, Newton, MA (US)

(73) Assignee: Minerva Biotechnologies Corporation, Waltham, MA (US)

( * ) Notice: Subject to any disclaimer, the term of this patent is extended or adjusted under 35 U.S.C. 154(b) by 346 days.

(21) Appl. No.: 09/971,056

(22) Filed: Oct. 3, 2001

(65) Prior Publication Data

US 2002/0098526 A1 Jul. 25, 2002

Related U.S. Application Data

(60) Provisional application No. 60/272,727, filed on Mar. 1, 2001, provisional application No. 60/237,427, filed on Oct. 3, 2000.

(51) Int. Cl.
*C12Q 1/68* (2006.01)
(52) U.S. Cl. .......................................................... 435/6
(58) Field of Classification Search .................... 435/6, 435/4, 7.1, 7.2, 7.4, 7.5, 7.8, 7.91–7.95, 283.1, 435/287.2, 287.3, 287.7, 287.8, 287.9, 288.1–288.7; 436/514–518, 523–535, 538–541; 422/50, 422/56–61, 68.1, 69, 70, 73
See application file for complete search history.

(56) References Cited

U.S. PATENT DOCUMENTS

| | | | |
|---|---|---|---|
| 4,313,734 A | 2/1982 | Leuvering | |
| 4,596,660 A | 6/1986 | Hou | |
| 4,744,760 A | 5/1988 | Molday | |
| 4,853,335 A | 8/1989 | Olsen et al. | |
| 4,859,612 A | 8/1989 | Cole et al. | |
| 4,879,220 A | 11/1989 | Mrsny et al. | |
| 4,888,248 A | 12/1989 | Hirai et al. | |
| 4,945,045 A | 7/1990 | Forrest et al. | |
| 5,135,627 A | 8/1992 | Soane | |
| 5,147,841 A | 9/1992 | Wilcoxon | |
| 5,177,012 A | 1/1993 | Kim et al. | |
| 5,248,772 A | 9/1993 | Siiman et al. | |
| 5,294,369 A | 3/1994 | Shigekawa et al. | |
| 5,384,073 A | 1/1995 | Shigekawa et al. | |
| 5,589,401 A | 12/1996 | Hansen et al. | |
| 5,595,649 A | 1/1997 | Markell et al. | |
| 5,620,820 A | 4/1997 | Bertrand et al. | |
| 5,620,850 A | 4/1997 | Bamdad et al. | |
| 6,001,231 A * | 12/1999 | Kopf-Sill | 204/454 |
| 6,001,556 A | 12/1999 | Charych et al. | |
| 6,180,084 B1 | 1/2001 | Ruoslahti et al. | |
| 6,188,812 B1 * | 2/2001 | Kao et al. | 385/12 |
| 6,245,270 B1 | 6/2001 | Mizutani et al. | |
| 6,288,220 B1 * | 9/2001 | Kambara et al. | 536/24.31 |
| 6,319,670 B1 * | 11/2001 | Sigal et al. | 435/6 |
| 6,342,349 B1 | 1/2002 | Virtanen et al. | |
| 6,346,389 B1 | 2/2002 | Altieri et al. | |
| 6,361,944 B1 * | 3/2002 | Mirkin et al. | 435/6 |
| 6,413,770 B1 | 7/2002 | Godowski et al. | |
| 6,417,340 B1 | 7/2002 | Mirkin et al. | |
| 6,440,645 B1 * | 8/2002 | Yon-Hin et al. | 430/322 |
| 6,495,324 B1 | 12/2002 | Mirkin et al. | |
| 6,586,193 B2 * | 7/2003 | Yguerabide et al. | 506/3 |
| 6,681,616 B2 * | 1/2004 | Spaid et al. | 73/54.07 |
| 2002/0006643 A1 | 1/2002 | Kayyem et al. | |
| 2002/0042074 A1 | 4/2002 | Bamdad et al. | |
| 2002/0086443 A1 | 7/2002 | Bamdad | |

(Continued)

FOREIGN PATENT DOCUMENTS

DE 199 18 486 A1 10/2000

(Continued)

OTHER PUBLICATIONS

Bamdad, Cynthia, "The Use of Variable Density Self-Assembled Monolayers to Probe the Structure of a Target Molocule," Biophysical Journal, Oct. 1998, vol. 75, pp. 1989-1996.

(Continued)

*Primary Examiner*—Ann Y Lam
(74) *Attorney, Agent, or Firm*—Joseph H. Kim; JHK Law

(57) ABSTRACT

Porous members can be positioned so as to partially or fully span channels in microfluidic systems. The porous members can be assembled and/or disassembled in situ. The porous members can be made such that pores are separated by connections including but a single molecule at one location, allowing for a high level of open area in a very small pore size member. The porous member can be made up of colloid particles interconnected with molecular species. These can be used to detect analytes qualitatively and/or quantitatively, or to selectively bind and/or release agents on command for a variety of purposes including first blocking, then opening a channel, concentrating analyte over time followed by release of analyte and detection downstream, etc. Porous members can define valves in multiple-channel systems and, with controlled binding and release of agents at the porous members, these valves can be opened and closed and fluid flow controlled in a multi-channel system. Fluidic systems of the invention can include multiple sensing locations at which different analytes are determined. Systems of the invention provide flexibility for overall microchemical analysis, sequentially, of a variety of agents.

58 Claims, 19 Drawing Sheets

U.S. PATENT DOCUMENTS

| | | | |
|---|---|---|---|
| 2002/0155462 | A1 | 10/2002 | Mirkin et al. |
| 2002/0156112 | A1 | 10/2002 | Bamdad et al. |
| 2002/0164611 | A1 | 11/2002 | Bamdad et al. |
| 2002/0172953 | A1 | 11/2002 | Mirkin et al. |
| 2002/0192687 | A1 | 12/2002 | Mirkin et al. |
| 2003/0036199 | A1 | 2/2003 | Bamdad et al. |

FOREIGN PATENT DOCUMENTS

| | | | |
|---|---|---|---|
| EP | 0 142 301 | A2 | 5/1985 |
| EP | 0 299 428 | A2 | 1/1989 |
| EP | 0 489 465 | B1 | 9/1996 |
| WO | WO 92/08134 | A1 | 5/1992 |
| WO | WO 96/29629 | A2 | 9/1996 |
| WO | WO 98/04740 | A | 2/1998 |
| WO | WO 98/20162 | A2 | 5/1998 |
| WO | WO 98/41572 | A | 9/1998 |
| WO | WO 00/43783 | A3 | 7/2000 |
| WO | WO 00/43791 | A2 | 7/2000 |
| WO | WO 01/78709 | A2 | 10/2001 |
| WO | WO 01/92277 | A1 | 12/2001 |
| WO | WO 02/01225 | A2 | 1/2002 |
| WO | WO 02/01228 | A2 | 1/2002 |
| WO | WO 02/01230 | A2 | 1/2002 |
| WO | WO 02/37109 | A2 | 5/2002 |
| WO | WO 02/39999 | A2 | 5/2002 |
| WO | WO 02/056022 | A2 | 7/2002 |
| WO | WO 02/061129 | A2 | 8/2002 |
| WO | WO 02/076248 | A2 | 10/2002 |

OTHER PUBLICATIONS

Bamdad, Cynthia Carol, "Novel Surfaces for the Detection and Study of Intermolecular Interactions," A thesis presented by Cynthia Carol Bamdad to the Committee for Higher Degrees in Biophysics in partial fulfillment of the requirements for the degree of Doctor of Philosophy in the subject of Biophysics, Harvard University, Cambridge, Massachusetts. May 1997. pp. I-111. UMI Dissertation Services, Ann Arbor, MI.

Baruch et al., "Preferential expression of novel MUC1 tumor antigen isoforms in human epithelial tumors and their tumor-potentiating function", Int J. Cancer, 1997, vol. 71, pp. 741-749.

Choi et al., "Labeling digoxin antibody with colloidal gold and ferrocene for its use in membrane immunostrip and immunosensor", *Microchemical Journal*, vol. 63, Sep. 1999, pp. 92-99.

Cox, Dp, "Cationic colloidal gold, a stain for anionic tissue sites", Am Biotechnol Lab, Oct. 1990, vol. 8, No. 12, p. 58, Abstract Only.

Gendler et al., "Molecular cloning and expression of human tumor-associated polymorphic epithelial mucin", The Journal of Biological Chemistry, 1990, vol. 265, No. 25, pp. 15286-15293.

Gugliucci et al., "Reaction of advanced glycation endproducts with renal tissue from normal and streptozotocin-induced diabetic rats: an ultrastructural study using colloidal gold cytochemistry.", Jun. 1995, J Histochem Cytochem, vol. 43, No. 6, pp. 591-600, Abstract Only.

Hacker et al., "Application of silver acetate autometallography in histopathology: a new detection methods for use in immunogold silver staining, lectin histochemistry and in situ hybridization.", VERH DTSCH GES. PATHOL., 1990, vol. 74, pp. 368-372, Abstract Only.

Hacker et al., "Electron microscopical autometallography: Immunogold-silver staining (IGSS) and heavy-metal histochemistry.", Methods, Oct. 1996, vol. 10, No. 2, pp. 257-269, Abstract only.

Hacker et al., "The use of silver acetate autometallography in the detection of catalytic tissue metals and colloidal gold particles bound to macromolecules.", Prog Histochem Cytochem, 1991, vol. 23, No. 1-4, pp. 286-290.

Ligtenberg et al., "Cell-associated episialin is a complex containing two proteins derived from a common precursor", The Journal of Biological Chemistry, 1992, vol. 267, No. 9, p. 6176-6177.

Ligtenberg et al., "Episialin, a carcinoma-associated mucin, is generated by a polymorphic gene encoding splice variants with alternative amino termini", The Journal of Biological Chemistry, 1990, vol. 265, No. 10, pp. 5573-5578.

Robinson et al., "Bioelectrochemical Enzyme Immunoassay of Human Choriogonadotropin with Magnetic Electrodes", *Clinical Chemistry*, vol. 31, No. 9, 1985, pp. 1449-1452.

Smorodinsky et al., "Detection of a secreted MUC1/SEC protein by MUC1 isoform specific monoclonal antibodies", Biochemical and Biophysical Research Communications, 1996, vol. 228, pp. 115-121.

Stirling, JW., "Unfixed tissue for electron immunocytochemistry: a simple preparation method for colloidal gold localization of sensitive epitopes using ethanediol dehydration.", Histochem J, Apr. 1992, vol. 24, No. 4, pp. 190-206, Abstract Only.

Tsuyama et al., "Mucin histochemistry of colonic mucous cells with lectin-colloidal gold complex.", J Electron Microsc 1985, vol. 34, No. 3, pp. 174-178., Tokyo.

Wreschner et al., "Human epithelial tumor antigen cDNA sequences—Differential splicing may generate multiple splicing forms", Europ J. Biochem, 1990. vol. 189, pp. 463-473.

Zrihan-Licht et al., "Characterization and molecular cloning of a novel MUC1 protein devoid of tandem repeats, expressed in human breast cancer tissue", Europ J. Biochem, 1994, vol. 224, pp. 787-795.

Bendayan et al., "Effect of tissue processing on colloidal gold CytoChemistry.", J. Histochem Cytochem, Sep. 1987, vol. 35, No. 9, pp. 983-996, Abstract Only.

Hisano et al., "Some improvement in tissue preparation and colloidal-gold immunolabeling for electron microscopy." Am J Anat, Feb.-Mar. 1986, vol. 175, No. 2-3, pp. 245-266, Abstract Only.

Danscher et al., "Light microscopic visualization of colloidal gold on resin-embedded tissue.", J. Histochem Cytochem, Dec. 1983, vol. 31, No. 12, pp. 1394-1398, Abstract Only.

Geuze et al., "Use of colloidal gold particles in double-labeling immunoelectron microscopy of ultrathin frozen tissue sections.", J Cell Biol, Jun. 1989, vol. 89, No. 3, pp. 653-665, Abstract Only.

Roth, J., "The silver anniversary of gold: 25 years of the colloidal gold marker system for immunocytochemistry and histochemistry", Histochem Cell Biol, Jul. 1996, vol. 106, No. 1, pp. 1-8, Abstract Only.

Dolapchieva, S., "Distribution of concanavalin A and wheat germ agglutinin binding sites in the rat peripheral nerve fibres revealed by lectin/glycoprotein-gold histochemistry.", Histochem J., Jan. 1996, vol. 28, No. 1, pp. 7-12, Abstract Only.

Roth et al., "Improved accuracy in diagnostic immunohistochemistry, lectin histochemistry and in situ hyridization using a gold-labeled horseradish peroxidase antibody and silver intensification.", Lab Invest, Aug. 1992, vol. 67, No. 2, pp. 263-269, Abstract Only.

Herken et al., "Postembedding immunogold histochemistry for the localization of laminin and its E4 and P1 fragments in mouse kidney embedded in LR-White and LR-Gold." Histochem J., Jun. 1991, vol. 23, No. 6, pp. 267-272, Abstract Only.

Jackson et al., "Application of 1 nm gold probes on paraffin wax sections for in situ hybridisation histochemistry." J Clin Pathol, Oct. 1990, vol. 43, No. 10, pp. 810-812, Abstract Only.

Cornelese-Ten et al., "New sensitive light microscopial detection of colloidal gold on ultrathin.", Histochemistry, 1990, vol. 94, No. 1, pp. 61-71, Abstract Only.

Herken et al., "Light and electron microscopial postembedding lectin histochemistry for WGA-binding sites in the renal cortex of the mouse embedded in polyhydroxy aromatic resins LR-White and LR-Gold", Histochemistry,1988, vol. 89, No. 3, pp. 277-282, Abstract Only.

Package inserts, Secondary antibody coated colloidal gold probes for used in the electron microscopial Immunogold (silver) straining technique, Auroprobe, codes RPN 420-436, RPN, 444; Jun. 8, 1999, Amersham, Piscataway, NJ, pp. 1-7.

\* cited by examiner

ELECTRONIC DETECTION OF INTERACTION AND DETECTION OF INTERACTION BASED ON THE INTERRUPTION OF FLOW

RELATED APPLICATIONS

This non-provisional application claims the benefit under Title 35, U.S.C. §119(e) of U.S. provisional application No. 60/237,427, filed Oct. 3, 2000 and U.S. provisional application No. 60/272,727, filed Mar. 1, 2001, each of which is incorporated by reference herein.

FIELD

The present invention relates to novel methods of detection based on the interruption of flow and methods to use this interruption of flow through a channel to redirect flow through a complex circuit of flow channels for detection relating to diagnostics, therapeutics, environmental sampling and food monitoring. The present invention also relates to methods of manipulating and handling samples, suspected of containing a target substance, including biological samples, to detect, separate and/or concentrate target materials such as molecules, biological molecules, cells and spores. The present invention can be utilized for or adapted to multiplexing processes and logical processes including manipulating flow paths and rates for the above detection and separation. The invention can also be utilized for detection in constant monitoring systems, which include but are not limited to, environmental monitoring, remote monitoring, food safety, and implantable biosensors.

BACKGROUND

There is currently great commercial interest in developing micro- and nano-scale biosensors for point of care diagnostics, lab-on-a-chip devices, and a variety of miniaturized sensors, including those designed to detect biological warfare agents. Virtually all of these applications require integrated sample preparation. Three processes are typically necessary for sample preparation: 1) filtering out debris that can clog micro-fluidic channels within devices and hinder the sensitivity of detection; 2) concentrating the target analyte to enhance sensitivity; and 3) releasing the target for downstream detection at a predictable position. There is currently no existing technology to accomplish these sample preparation processes in a chip-scale device. Conventional filters and sample concentrators are impractical because they are constructed of membrane-like materials that require large pressure gradients to force a sample through their small effective diameters open to fluid flow. Standard sample preparation filters are typically nitrocellulose membranes that have about a 0.2 micron nominal pore size. The combined cross-sectional area of the pores in one of these filters is typically only about 0.3% of the total cross-sectional area of the filter. This means that the effective diameter of the flow channel in which the filter is present is greatly reduced by the presence of the filter. The pressure required to force a sample through a flow channel is inversely proportional to the fourth power of the flow channel diameter. Thus, this reduction in effective flow channel diameter can translate into a large pressure drop and resulting upstream pressure requirement that cannot currently be incorporated into a chip-scale device. Large pressure drops, which are easily generated on bench-top instruments, such a micro centrifuges, cannot be easily generated within micro-devices. Currently, macro-scale, off-line pumps separate from the micro-device are typically required to pass sample fluids through filters in micro-scale biosensors or other micro-scale devices.

Another impediment to integrating standard sample preparation components into chip-scale sensors is reusability. Currently available filters are typically single-use, non-reusable components, which, if integrated into chip-scale biosensors, would render these expensive devices single-use and non-reusable. Additionally, integration of such components would require the use of connectors, which in the micro-scale, have been plagued with leakage and rupture problems.

SUMMARY OF THE DISCLOSURE

Many of the above limitations and problems of the screening and determining of target substances such as biological material, are addressed in the present inventive system.

The present disclosure describes porous members that, in preferred embodiments, can comprise 3-dimensional net-like nanostructures (or "nano-nets"), comprised of interconnecting nanoparticles and polymers, which can be self-assembled to span flow channels to form nano-scale filters, concentrators and/or in situ detectors that detect the capture of a target substance or pathogen by detecting an interruption of flow through a channel. The invention addresses the problem of how to perform sample preparation in a miniaturized sensor. The present invention can solve some critical problems, detailed below, that plague the development of miniaturized sensors by providing low pressure-drop filters and concentrators that are also reconfigurable. These methods are especially suitable for real-time, continuous monitoring used in remote sensing as well as in implantable devices.

Aspects of the invention describe the use of derivatized nanoparticles and biopolymers to assemble multifunctional, reusable/regeneratable three-dimensional nanostructures that can be assembled in micro- or nano-scale flow channels to create novel biosensors, nano-filters and nano-concentrators.

The porous members or nanostructures can also function as biosensors when the suspended nano-particles are derivatized to present a recognition ligand for a target substance. The capture of the target species can be detected by detecting changes in downstream pressure, flow rate or other parameters, which result from interruption of flow.

The present invention also describes porous members comprising nano-filters, made up of interconnecting particles and polymers, preferably biopolymers, that are assembled in situ within the flow channel so that they become an integral part of the channel. As some examples, a nano-filter, e.g. constructed from DNA and colloidal gold nanoparticles, can provide an equivalent nominal or average pore size of less than 0.5 micron, in other embodiments less than 0.2 micron, in other embodiments less than 100 nanometers (nm), in other embodiments less than 50 nm, in other embodiments less than 10 nm, and in other embodiments less than 5 nm, and can present at least about 50%, more preferably at least about 70%, more preferably at least about 80%, more preferably at least about 90%, more preferably at least about 95%, and in some embodiments as much as 98% or more, of the cross-sectional area open to flow compared to about 0.3% presented by typical standard membrane filters. This increase in the effective flow channel diameter can result in at least a 16-fold decrease, in other embodiments at least a 250-fold decrease, in other embodiments at least a 600-fold decrease, in other embodiments at least a 10,000-fold decrease, in yet other embodiments at least a 100,000-fold decrease in the pressure required to maintain a given rate of flow through the channel. Such resulting minimal pressure requirements can readily be generated by chip-scale pumps or even by a beating heart in an implantable device. Nanostructures that incorporate particles and biopolymers but do not include ligands that bind a target species are preferred for use as chip-scale filters, such filters can also be disassembled and reconfigured in situ, across interior cross-sections of flow channels. These structures can allow the filtering of a sample fluid at a given fluid flow at pressures that are orders of magnitude lower than those required by standard filters. The length of the interconnecting polymer strands can be altered to create nano-filters of varying effective nominal "pore" size to accommodate the exclusion of cells, spores, cellular debris, or bacteria or for other filtering applications. The nano-filters described in the present invention can be anchored to derivatized flow channels via biospecific interactions, such as DNA hybridization and/or biotin-streptavidin binding. Thus, the nano-filters can be dissociated, reassembled and reconfigured in situ for subsequent assays by simply disrupting the biological interactions that anchor them to the flow channel, followed by conditions allowing the nano-structures to reform.

Colloids derivatized to bear biospecific probes/ligands can, in some embodiments, be incorporated into the nano-filters described above to create nano-scale concentrators to capture, concentrate, then release specific target species. In yet another embodiment, such derivatized nano-nets can be used for target detection. The present invention, in some embodiments, involves the formation of nano-nets and use of these nano-nets to detect the presence of a target analyte in a fluid sample by detecting the interruption of flow through a channel following the capture of the target in the nano-net. The nano-nets in such embodiments can function as in situ sensors or biosensors when they trap target analytes and interrupt flow in the channel, by altering their effective cross-sectional area open to flow upon capture of the analytes. The presence of a target species in such embodiments can be detected when changes in flow rate, pressure drop and/or electro-osmotic forces across the flow channel caused by the interruption of flow are detected. Detection of a target species facilitated by detecting changes in the pressure drop across a flow channel according to the invention can be highly sensitive to the degree of interruption because the upstream pressure required to maintain a given flow rate through a channel is inversely proportional to the fourth power of the effective diameter of the channel. To enhance this detection ability even further, the topology of the flow channel can be constructed to have a tongue and groove configuration.

We have previously described in International patent application serial number PCT/US00/01997, filed Jan. 25 2000 by Bamdad et al., entitled "Rapid and Sensitive Detection of Aberrant Protein Aggregation in Neurodegenerative Diseases" (published as WO 00/43791 on Jul. 27 2000), International patent application serial number PCT/US00/01504, filed Jan. 21, 2000 by Bamdad, et al, entitled "Interaction of Colloid-Immobilized Species with Species on Non-Colloidal Structures" (published as WO 00/43783 on Jul. 27 2000), commonly-owned, copending U.S. patent application Ser. No. 09/602,778, filed Jun. 23 2000 by Bamdad et al., entitled "Interaction of Colloid-Immobilized Species with Species on Non-Colloidal Structures"; and commonly-owned, copending U.S. patent application Ser. No. 09/631,818, filed Aug. 3, 2000 by Bamdad et al., entitled "Rapid and Sensitive Detection of Protein Aggregation" (all incorporated herein by reference), methods for the formation of biospecific self-assembled monolayers (SAMs) on gold colloids. These methods enable the presentation of DNA, proteins, peptides, antibodies, other ligands, or combinations of these, on nanoparticles. In one embodiment, the invention provides nano-nets that are constructed from polymers connected to nanoparticles that present an antibody against a target pathogen or analyte. In such embodiments, the nano-net comprises a specific concentrator and/or detector of that analyte.

In another preferred embodiment, a flow system can be arranged to form a logical flow path including valves that can re-direct flow within the system under the control of a computer system or other control system. The determination of a configuration of an actual flow path within the system can be configured to be dependent upon what target(s) has or what has not been detected most recently at one or more detection sites. For example, the capture of a target analyte at a specific location along a flow path can impede flow along that flow path, which, in turn, can be utilized to detect the presence of the target analyte and to re-direct flow within the system in a logical manner such that logical sequential detection and thus diagnostics can be accomplished.

For a better understanding of the present invention, together with other and further objects thereof, reference is made to the accompanying drawings and detailed description.

In one aspect the invention provides a series of articles. One article includes a channel able to contain a flowing fluid, and a porous member at least partially spanning the channel. The porous member comprises a colloid particle.

In another embodiment, the invention involves an article including a channel able to contain a flowing fluid, and a porous member at least partially spanning the channel where the porous member includes at least two pores separated by a single molecule. This does not necessarily mean that the two pores are separated, along their entire boundary, by a single molecule. It means that at at least one point in the structure separating the two pores, a single molecule separates the two pores, and cleavage of that single molecule would cause the two pores to become one.

In another embodiment, an article includes a channel able to contain a flowing fluid and a porous member at least partially spanning the channel, where the porous member has an average pore size of less than 1 micron and an area open to flow of at least 50%. By "area open to flow" of at least a particular percentage is meant, of course, that the area of the channel spanned by the porous member is blocked less than (100 minus that percentage)%.

In another aspect, the invention provides a series of methods. One method involves passing a fluid through a porous member and allowing a chemical, biological, or biochemical agent within the fluid to bind to a binding partner of the agent immobilized relative to the porous member. This binding is determined, according to the method.

In another embodiment, a method of the invention involves replacing a first binding partner of a chemical, biological, or biochemical agent immobilized relative to a porous member, at least partially spanning a fluid flow channel, with a second binding partner. The replacement is conducted without disassembling the porous member relative to the channel.

Another method of the invention involves passing a fluid through a porous member and allowing a chemical, biological, or biochemical agent within the fluid to bind to a binding partner of the agent immobilized relative to the porous member. The chemical, biological, or biochemical agent is then released from the porous member.

In another embodiment, a method involves allowing a first chemical, biological, or biochemical agent to become immobilized relative to a first colloid particle. A second chemical, biological, or biochemical agent is allowed to become immobilized relative to a second colloid particle. Based at least in part of the identity of the first and second agents, the first colloid particle is directed to a first fluid channel and the second colloid particle is directed to a second fluid channel.

Another method of the invention involves allowing a chemical, biological, or biochemical agent to become immobilized relative to a colloid particle and determining at least one characteristic of the agent. Based at least in part on the characteristic, the colloid particle is directed to a first fluid channel rather than a second fluid channel. Each channel is capable of receiving the colloid particle prior to the directing step. Another method of the invention involves allowing a chemical, biological, or biochemical agent to become immobilized relative to a colloid particle, determining at least one characteristic of the agent at a first detection location, and determining at least one characteristic of the agent at a second detection location.

Another method of the invention involves determining the identity of a chemical, biological, or biochemical agent by determining the flow path of a fluid, initially containing the agent, where the fluid has a plurality of flow path options.

In connection with any of the aspects or embodiments of the invention described above or elsewhere in the present application, the following characteristics of components or method steps, to the extent that these components or method steps are involved in those aspects or embodiments, can apply. Where a channel is involved, the channel can have a cross-sectional dimension of less than about 1000 microns, or less than about 500, 300, 100, or 50 microns in other embodiments. Where a porous member spans a channel, it can span a portion of the channel or can completely span the channel. Where the porous member partially spans the channel, some fluid flowing through the channel will flow through the porous member but other fluid can pass by the porous member and not flow through it. Where the porous member completely spans the channel, any fluid flowing within the channel must pass through the porous member, i.e., the fluid cannot bypass the porous member within the channel.

Porous members of the invention can have an average pore size of less than 0.5 micron or, in other embodiments, less than 0.2 micron, less than 100 nanometers, less than 50 nanometers, less than 10 nanometers, or less than 5 nanometers.

The porous member can comprise a network of colloid particles interconnected with molecular species. The molecular species can be fastened to the colloid particles via affinity tag/recognition entity pairs. In some embodiments, at least some colloid particles are interconnected with other colloid particles via connections where each connection includes, at at least one point in the connection, a single molecule. This means that the connection between the colloid particles can include one or multiple molecules at a variety of locations, but at at least one point the connection defines only a single molecule, and rupture of that single molecule would separate the colloid particles. In some embodiments, an entire porous member that completely spans a channel is made up of colloid particles interconnected to other colloid particles via connections, all of which connections include, at at least one point in the connection, a single molecule. The colloid particles can be interconnected via molecules that are polymers, including synthetic or naturally-occurring polymers (such as peptides) and preferably oligonucleotides.

Porous members of the invention can have an open area of at least 70%, 80%, 90%, 95% or 98% in a variety of embodiments.

Channels can be defined by essentially any channel known to those skilled in the art. For example, the channel can be defined by a groove formed in a substrate, or the channel can be completely enclosed. That is, it can be an elongated, enclosed structure having an inlet and an outlet.

Some methods of the invention involve determining binding of a chemical, biological, or biochemical agent to its binding partner. In some embodiments, this binding can be determined qualitatively, and in other embodiments quantitatively. "Qualitatively" and "quantitatively", as used herein, are given their ordinary meaning in the art. "Qualitatively" means that whether or not one or more agents is present (e.g. has or have bound) is determined. "Quantitatively" means that the amount of agent (e.g. bound agent) is determined.

In one embodiment, a fluid flows along a main flow, and some but not all of the fluid is diverted from the main flow into an analysis flow. In the analysis flow, a determination is made as to binding between a chemical, biological, or biochemical agent and its binding partner. This determination can be used to affect the flow of fluid in the main channel. For example, in a public water supply where a pathogen is desirably excluded, an analysis flow can be diverted from a main water flow and continuously monitored to determine whether the pathogen is present by providing a binding partner of the pathogen immobilized on a porous member. If the pathogen is present and binds to the porous member, the porous member becomes partially or fully blocked, and the fluid pressure differential across the porous member changes. This can be detected as a signal used to reduce or shut down the main fluid flow.

In some embodiments, chemical, biological, or biochemical agent is allowed to bind at a porous member and thereby collected at the porous member. The agent then is released at a desired point in time and detected downstream. In this manner, the porous member is used to collect, over time, the agent and then to release the agent all at once (or at least in a shorter period of time than the period of time during which it is collected). This can allow very sensitive detection of very low levels of agent by concentrating the agent over time, then releasing the concentrated agent and detecting it.

Other advantages, novel features, and objects of the invention will become apparent from the following detailed description of the invention when considered in conjunction with the accompanying drawings, which are schematic and which are not intended to be drawn to scale. In the figures, each identical, or substantially similar component that is illustrated in various figures is represented by a single numeral or notation. For purposes of clarity, not every component is labeled in every figure, nor is every component of each embodiment of the invention shown where illustration is not necessary to allow those of ordinary skill in the art to understand the invention.

DETAILED DESCRIPTION

Definitions

Figure 1:
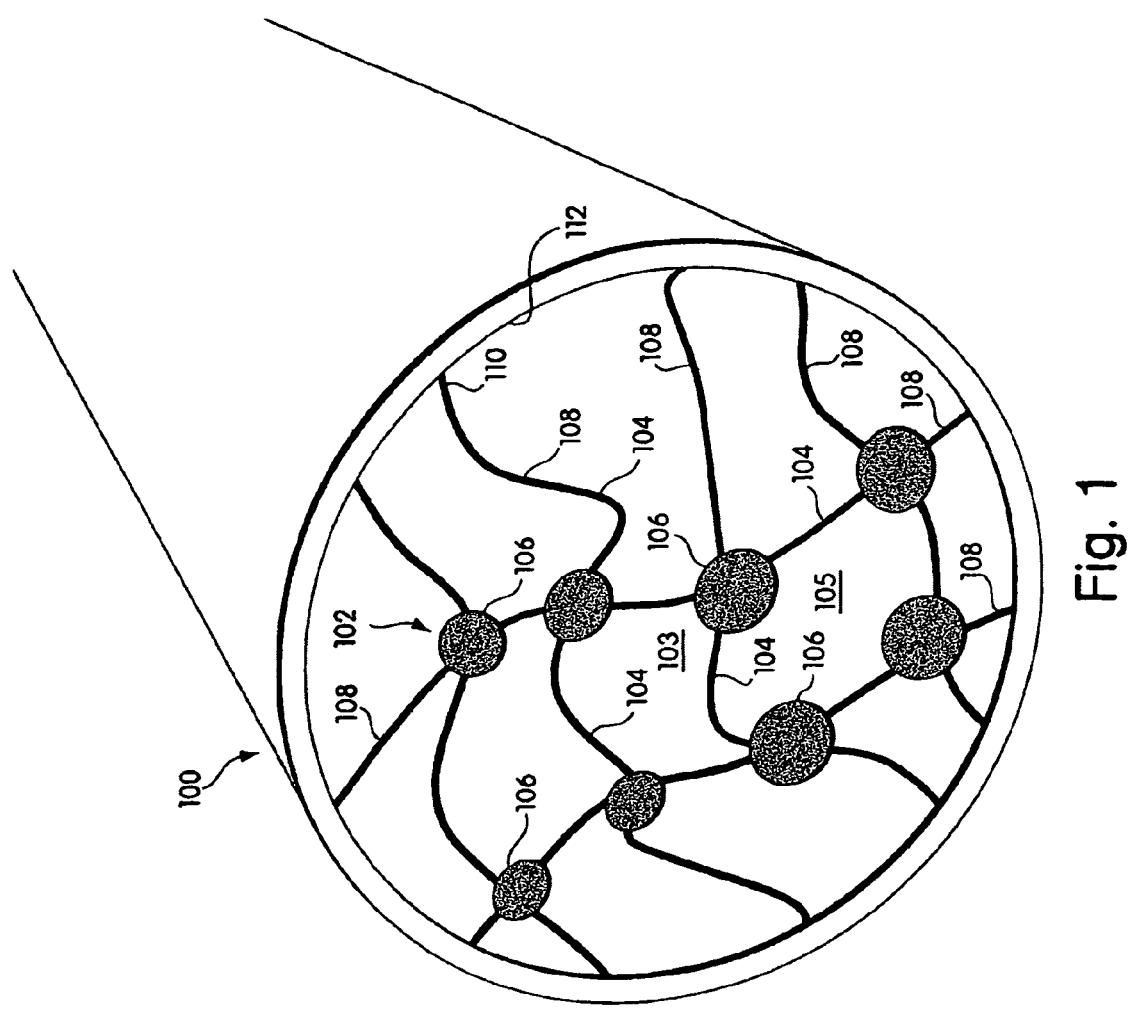
FIG. 1 is a schematic illustration of a self-assembled nanostructure, comprised of interconnecting polymers attached to functionalized nanoparticles, which is anchored to the interior of a flow channel via interaction with a functional groups on the flow channel surface, according to one embodiment of the invention.

"Small molecule", as used herein, means a molecule less than 5 kiloDalton, more typically less than 1 kiloDalton. As used herein, "small molecule" excludes proteins.

The term "candidate drug" as used herein, refers to any medicinal substance used in humans, animals, or plants. Encompassed within this definition are compound analogs, naturally occurring, synthetic and recombinant pharmaceuticals, hormones, antimicrobials, neurotransmitters, etc. This includes any substance or precursor (whether naturally occurring, synthetic or recombinant) which is to be evaluated for use as a drug for treatment of neurodegenerative disease, or other disease characterized by aberrant aggregation, or prevention thereof. Evaluation typically takes place through activity in an assay, such as the screening assays of the present invention.

A variety of types of particles can be used in the invention. For example, particles utilized within the scope of the invention can include one or more of the following: a "fluid suspendable particle" meaning a particle that can be made to stay in suspension in a fluid in which it is used for purposes of the invention (typically an aqueous solution) by itself, or can be maintained in solution by application of a magnetic field, an electromagnetic field, agitation such as stirring, shaking, vibrating, sonicating, centrifuging, vortexing, or the like; a "magnetically suspendable" particle being one that can be maintained in suspension in a fluid via application of a magnetic field; an electromagnetically-suspendable particle being one that can be maintained in suspension in a fluid by application of an electromagnetic field (e.g., a particle carrying a charge, or a particle modified to carry a charge); a "self-suspendable particle" being a particle that is of low enough size and/or mass that it will remain in suspension in a fluid in which it is used (typically an aqueous solution), without assistance of for example a magnetic field, for at least 1 hour. Other self-suspendable particles will remain in suspension, without assistance, for 5 hours, 1 day, 1 week, or even 1 month, in accordance with the invention.

"Proteins" and "peptides" are well-known terms in the art, and are not precisely defined in the art in terms of the number of amino acids that each includes. As used herein, these terms are given their ordinary meaning in the art. Generally, peptides are amino acid sequences of less than about 100 amino acids in length, but can include sequences of up to 300 amino acids. Proteins generally are considered to be molecules of at least 100 amino acids.

As used herein, a "metal binding tag" refers to a group of molecules that can become fastened to a metal that is coordinated by a chelate. Suitable groups of such molecules include amino acid sequences, typically from about 2 to about 10 amino acid residues. These include, but are not limited to, histidines and cysteines ("polyamino acid tags"). Such binding tags, when they include histidine, can be referred to as a "poly-histidine tract" or "histidine tag" or "HIS-tag", and can be present at either the amino- or carboxy-terminus, or at any exposed region, of a peptide or protein or nucleic acid. A poly-histidine tract of six to ten residues is preferred for use in the invention. The poly-histidine tract is also defined functionally as being a number of consecutive histidine residues added to a protein of interest which allows the affinity purification of the resulting protein on a metal chelate column, or the identification of a protein terminus through the interaction with another molecule (e.g. an antibody reactive with the HIS-tag). It should be understood that reference to a particular type of metal binding tab below, for example a histidine tag, is merely exempleary and that such tag could, alternatively, comprise any of the above metal binding tags.

"Affinity tag" is given its ordinary meaning in the art. Affinity tags include, for example, metal binding tags, GST (in GST/glutathione binding clip), and streptavidin (in biotin/steptavidin binding). At various locations herein specific affinity tags are described in connection with binding interactions with complementary recognition entity pairs. It is to be understood that the invention involves, in any embodiment employing an affinity tag, a series of individual embodiments each involving selection of any of the affinity tags described herein.

As used herein, "chelate coordinating a metal" or metal coordinated by a chelate, refers to a metal coordinated by a chelating agent that does not fill all available coordination sites on the metal, leaving some coordination sites available for binding via a metal binding tag. U.S. Pat. No. 5,620,850 of Bamdad, et al., incorporated herein by reference, describes exemplary metal binding tag/chelate linkages.

"Signaling entity" means an entity that is capable of indicating its existence in a particular sample or at a particular location. Signaling entities of the invention can be those that are identifiable by the unaided human eye, those that may be invisible in isolation but may be detectable by the unaided human eye if in sufficient quantity (e.g., colloid particles), entities that absorb or emit electromagnetic radiation at a level or within a wavelength range such that they can be readily detected visibly (unaided or with a microscope including an electron microscope or the like), or spectroscopically, entities that can be detected electronically or electrochemically, such as redox-active molecules exhibiting a characteristic oxidation/reduction pattern upon exposure to appropriate activation energy ("electronic signaling entities"), or the like. Examples include dyes, pigments, electroactive molecules such as redox-active molecules, fluorescent moieties (including, by definition, phosphorescent moieties), up-regulating phosphors, chemiluminescent entities, electrochemiluminescent entities, or enzyme-linked signaling moieties including horse radish peroxidase and alkaline phosphatase. "Precursors of signaling entities" are entities that by themselves may not have signaling capability but, upon chemical, electrochemical, electrical, magnetic, or physical interaction with another species, become signaling entities. An example includes a chromophore having the ability to emit radiation within a particular, detectable wavelength only upon chemical interaction with another molecule. Precursors of signaling entities are distinguishable from, but are included within the definition of, "signaling entities" as used herein.

As used herein, "fastened to or adapted to be fastened", or "attached to or adapted to be attached" in the context of a species relative to another species or to a surface of an article, means that the species is chemically or biochemically linked via covalent attachment, attachment via specific biological binding (e.g., biotin/streptavidin), coordinative bonding such as chelate/metal binding, or the like. For example, "fastened" or "attached" in this context includes multiple chemical linkages, multiple chemical/biological linkages, etc., including, but not limited to, a binding species such as a peptide synthesized on a polystyrene bead, a binding species specifically biologically coupled to an antibody which is bound to a protein such as protein A, which is covalently attached to a bead, a binding species that forms a part (via genetic engineering) of a molecule such as GST or Phage, which in turn is specifically biologically bound to a binding partner covalently fastened to a surface (e.g., glutathione in the case of GST), etc. As another example, a moiety covalently linked to a thiol is adapted to be fastened to a gold surface since thiols bind gold covalently. Similarly, a species carrying a metal binding tag is adapted to be fastened to a surface that carries a molecule covalently attached to the surface (such as thiol/gold binding) which molecule also presents a chelate coordinating a metal. A species also is adapted to be fastened to a surface if a surface carries a particular nucleotide sequence, and the species includes a complementary nucleotide sequence.

"Covalently fastened" means fastened via nothing other than one or more covalent bonds. E.g. a species that is covalently coupled, via EDC/NHS chemistry, to a carboxylate-presenting alkyl thiol which is in turn fastened to a gold surface, is covalently fastened to that surface.

"Non-specific binding", as used herein, is given its ordinary meaning in the field of biochemistry.

"Colloids", as used herein, means nanoparticles, i.e. very small, self-suspendable or fluid-suspendable particles including those made of material that is, e.g., inorganic or organic, polymeric, ceramic, semiconductor, metallic (e.g. gold), non-metallic, crystalline, amorphous, or a combination. Typically, colloid particles used in accordance with the invention are of less than 250 nm cross section in any dimension, more typically less than 100 nm cross section in any dimension, and in most cases are of about 2-30 nm cross section. One class of colloids suitable for use in the invention is 10-30 nm in cross section, and another about 2-10 nm in cross section. As used herein this term includes the definition commonly used in the field of biochemistry.

The term "sample" refers to any cell, tissue, or fluid from a biological source (a "biological sample", or any other medium, biological or non-biological, that can advantageously be evaluated in accordance with the invention including, but not limited to, a biological sample drawn from a human patient, a sample drawn from an animal, a sample drawn from food designed for human consumption, a sample including food designed for animal consumption such as livestock feed, milk, an organ donation sample, a sample of blood destined for a blood supply, a sample from a water supply, or the like. One example of a sample is a sample drawn from a human or animal to whom a candidate drug has been given to determine the efficacy of the drug.

A "sample suspected of containing" a particular component means a sample with respect to which the content of the component is unknown. For example, a fluid sample from a human suspected of having a disease, such as a neurodegenerative disease or a non-neurodegenerative disease, but not known to have the disease, defines a sample suspected of containing neurodegenerative disease aggregate-forming species. "Sample" in this context includes naturally-occurring samples, such as physiological samples from humans or other animals, samples from food, livestock feed, etc., as well as "structurally predetermined samples", which are defined herein to mean samples, the chemical or biological sequence or structure of which is a predetermined structure used in an assay designed to test whether the structure is associated with a particular process such as a neurodegenerative disease. For example, a "structurally predetermined sample" includes a peptide sequence, random peptide sequence in a phage display library, and the like. Typical samples taken from humans or other animals include cells, blood, urine, ocular fluid, saliva, cerebro-spinal fluid, fluid or other samples from tonsils, lymph nodes, needle biopsies, etc.

"Molecular wires" as used herein, means wires that enhance the ability for a fluid encountering a SAM-coated electrode to communicate electrically with the electrode. This includes conductive molecules or, as mentioned above and exemplified more fully below, molecules that can cause defects in the SAM allowing communication with the electrode. A non-limiting list of additional molecular wires includes 2-mercaptopyridine, 2-mercaptobenzothiazole, dithiothreitol, 1,2-benzenedithiol, 1,2-benzene-dimethanethiol, benzene-ethanethiol, and 2-mercaptoethyl-ether. Conductivity of a monolayer can also be enhanced by the addition of molecules that promote conductivity in the plane of the electrode. Conducting SAMs can be composed of, but are not limited to: 1) poly (ethynylphenyl) chains terminated with a sulfur; 2) an alkyl thiol terminated with a benzene ring; 3) an alkyl thiol terminated with a DNA base; 4) any sulfur terminated species that packs poorly into a monolayer; 5) all of the above plus or minus alkyl thiol spacer molecules terminated with either ethylene glycol units or methyl groups to inhibit non specific adsorption. Thiols are described because of their affinity for gold in ready formation of a SAM. Other molecules can be substituted for thiols as known in the art from U.S. Pat. No. 5,620,820, and other references. Molecular wires typically, because of their bulk or other conformation, creates defects in an otherwise relatively tightly-packed SAM to prevent the SAM from tightly sealing the surface against fluids to which it is exposed. The molecular wire causes disruption of the tightly-packed self-assembled structure, thereby defining defects that allow fluid to which the surface is exposed to communicate electrically with the surface. In this context, the fluid communicates electrically with the surface by contacting the surface or coming in close enough proximity to the surface that electronic communication via tunneling or the like, can occur.

The term "biological binding" refers to the interaction between a corresponding pair of molecules that exhibit mutual affinity or binding capacity, typically specific or non-specific binding or interaction, including biochemical, physiological, and/or pharmaceutical interactions. Biological binding defines a type of interaction that occurs between pairs of molecules including proteins, nucleic acids, glycoproteins, carbohydrates, hormones and the like. Specific examples include antibody/antigen, antibody/hapten, enzyme/substrate, enzyme/inhibitor, enzyme/cofactor, binding protein/substrate, carrier protein/substrate, lectin/carbohydrate, receptor/hormone, receptor/effector, complementary strands of nucleic acid, protein/nucleic acid repressor/inducer, ligand/cell surface receptor, virus/ligand, etc.

The term "binding partner" refers to a molecule that can undergo binding with a particular molecule. Biological binding partners are examples. For example, Protein A is a binding partner of the biological molecule IgG, and vice versa.

The term "determining" refers to quantitative or qualitative analysis of a species via, for example, spectroscopy, ellipsometry, piezoelectric measurement, immunoassay, electrochemical measurement, and the like. "Determining" also means detecting or quantifying interaction between species, e.g. detection of binding between two species.

The term "self-assembled monolayer" (SAM) refers to a relatively ordered assembly of molecules spontaneously chemisorbed on a surface, in which the molecules are oriented approximately parallel to each other and roughly perpendicular to the surface. Each of the molecules includes a functional group that adheres to the surface, and a portion that interacts with neighboring molecules in the monolayer to form the relatively ordered array. See Laibinis, P. E.; Hickman, J.; Wrighton, M. S.; Whitesides, G. M. *Science* 245, 845 (1989), Bain, C.; Evall, J.; Whitesides, G. M. *J. Am. Chem. Soc.* 111, 7155-7164 (1989), Bain, C.; Whitesides, G. M. *J. Am. Chem. Soc.* 111, 7164-7175 (1989), each of which is incorporated herein by reference.

The term "self-assembled mixed monolayer" refers to a heterogeneous self-assembled monolayer, that is, one made up of a relatively ordered assembly of at least two different molecules.

The term "interruption" or "interrupt", when used in the context of flow through a flow channel refers to any increase in the resistance to flow through the flow channel caused by a reduction in the fraction of the cross-sectional area of the flow channel open to fluid flow, which reduction being caused, for example, by a presence of, or change in configuration in, a nano-structure or nano-net within at least a portion of the flow channel, thereby decreasing the effective diameter of the flow channel.

The term "effective diameter," when used in the above context, refers to the cross-sectional diameter of a hypothetical flow channel having a cross section completely open to fluid flow and providing a resistance to fluid flow that is essentially equal to the resistance of a flow channel having a restriction therein, for example, a nano-net, causing an interruption of flow through the flow channel, and wherein the hypothetical flow channel has an overall cross-sectional shape substantially similar to that of the actual restricted flow channel.

In one aspect of the invention, three-dimensional, biospecific lattices are self-assembled from particles and interconnecting polymers (e.g., natural and/or synthetic polymers) across flow channels and are used to perform sample preparation, and/or concentration and detection of target analytes in chip-scale devices. The particles preferably bear moieties that facilitate their attachment to the polymer to form a polymer network. In another embodiment, the particles can also bear probe ligands that capture a target substance for example, by biologically binding to the target substance. The interconnected polymer/particle network formed, as described above, define resulting nanostructures which can be used as ultra low-pressure drop filters, target analyte concentrators, in situ biodetectors, or for a variety of other purposes. These structures can also be used, in some embodiments, to inhibit or block flow through a channel to act as a logical or reconfigurable valve.

FIG. 1 is a schematic illustration showing a flow channel 100 including therein, and spanning cross section thereof, a self-assembled porous member comprising nanostructure 102 comprised of segments of polymers 104 attached to and interconnecting functionalized nanoparticles 106. Certain polymer chains at the periphery of the nanostructure, for example, 108, have a terminal end, e.g., 110, which is attached to the interior 112 of flow channel 100, for example, via interaction with one or more functional groups on surface 112 of the flow channel. As illustrated in FIG. 1, a feature of many of the the porous members comprising nanostructures or nano-nets of the present invention is that the nanoparticles are interconnected to each other via a series of individual connections (e.g. 104) that include, at at least one point along the length of the connection only a single molecule (e.g. a single biopolymer or synthetic polymer chain). Furthermore, the inventive porous members comprising nanostructures or nano-nets can include two adjacent pores, e.g. pores 103 and 105 of FIG. 1, which are separated by the width of only a single molecule, e.g. 104.

In one embodiment, the particles are nanoparticles and/or self-suspendable particles and the polymer is a biopolymer (for example, a protein or peptide, polysaccharite, and/or nucleic acid) and the attachments connecting the particles and biopolymers/flow channel surface are mediated by biological binding. In a preferred embodiment, the nanoparticles are colloidals and the biopolymer is DNA. In an especially preferred embodiment, gold colloids, that have been derivatized with self-assembled monolayers (SAMs), are connected by strands of DNA that present binding partners to moieties displayed on the colloids and on the interior surface of the flow channel. The interaction between such moieties on colloids and binding partners on DNA can be designed to be reversible or irreversible. The mechanism of binding can be DNA-DNA hybridization, other biological binding, or chemical coupling, (discussed below in greater detail in FIG.

6 and associated description). Reversible binding mechanisms can allow for reconfiguration of the nanostructure. For example, DNA-DNA interactions can be disrupted by exposure of the DNA to heated water to release the interactions supporting the nano-structure. For embodiments utilizing protein-protein biological binding, such binding interactions can be released, for example, by introduction of chemicals such as urea or detergents or via changes in pH. Proper conditions and disrupting agents can readily be selected to effect reconfigurations and/or release of binding interactions to permit, for example, complete collapse the nanostructure to release all substances immobilized thereto, for example for downstream analysis or detection, or, in other embodiments, to replace a first binding partner immobilized to the nanostructure with a second binding partner, without disassembly of the network forming the nanostructure, or to release an analyte from a binding partner immobilized to the nanostructure without disassembly of the network forming the nanostructure, for downstream determination of the analyte, etc.

Certain embodiments of the invention make use of self-assembled monolayers (SAMs) on surfaces, such as surfaces of colloid particles, and articles such as colloid particles having surfaces coated with SAMs. In one set of preferred embodiments, SAMs formed completely of synthetic molecules completely cover a surface or a region of a surface, e.g. completely cover the surface of a colloid particle. "Synthetic molecule", in this context, means a molecule that is not naturally occurring, rather, one synthesized under the direction of human or human-created or human-directed control. "Completely cover" in this context, means that there is no portion of the surface or region that directly contacts a protein, antibody, or other species that prevents complete, direct coverage with the SAM. I.e. the surface or region includes, across its entirety, a SAM consisting completely of non-naturally-occurring molecules (i.e. synthetic molecules). The SAM can be made up completely of SAM-forming species that form close-packed SAMs at surfaces, these species in combination with molecular wires or other species able to promote electronic communication through the SAM (including defect-promoting species able to participate in a SAM), other species able to participate in a SAM, and any combination of these. Preferably, all of the species that participate in the SAM include a functionality that binds, optionally covalently, to the surface, such as a thiol which will bind to a gold surface covalently. A self-assembled monolayer on a surface, in accordance with the invention, can be comprised of a mixture of species (e.g. thiol species when gold is the surface) that can present (expose) essentially any chemical or biological functionality. For example, they can include tri-ethylene glycol-terminated species (e.g. tri-ethylene glycol-terminated thiols) to resist non-specific adsorption, and other species (e.g. thiols) terminating in a binding partner of an affinity tag, e.g. terminating in a chelate that can coordinate a metal such as nitrilotriacetic acid which, when in complex with nickel atoms, captures histidine-tagged binding species. These arrangements can be used for a variety of embodiments of the invention. As an example, a self-assembled monolayer, whether formed on a colloid or on another surface, can be comprised of a mixture of thiol species (when gold is the surface) that include tri-ethylene glycol-terminated thiols to resist non-specific adsorption and thiols terminating in a binding partner of an affinity tag, e.g. terminating in a chelate that can coordinate a metal such as nitrilo tri-acetic acid which, when in complex with nickel atoms, capture histidine-tagged binding species. The present invention provides, in certain embodiments, a method for rigorously controlling the concentration of essentially any chemical or biological species presented on a colloid surface, for example for forming various 3-dimensional nanostructures according to the invention.

Figure 2:
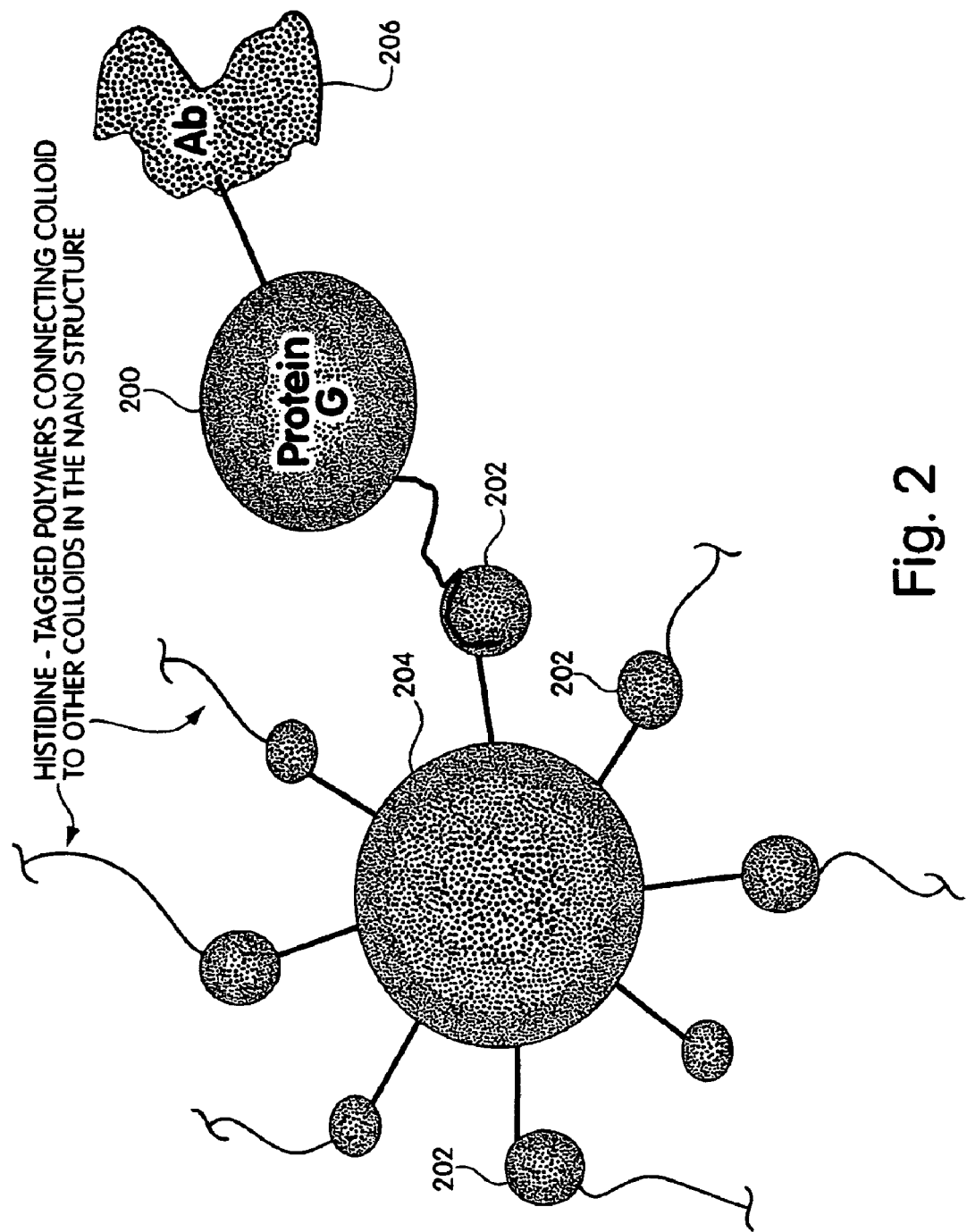
FIG. 2 is a schematic illustration showing an antibody attached to a nanoparticle of a nanostructure, according to one embodiment of the invention, via an interaction with a fragment of Protein G, which, is in turn bound to the nanoparticle through an interaction between its histidine-tag and an NTA-Ni(II) moiety presented on the nanoparticle.

In one aspect of the invention, 3-dimensional structures are formed in situ across flow channels. The invention is particularly well suited to the formation of nanostructures spanning partially, and preferably completely, across micro- and nano-flow channels (e.g., those having at least one cross-sectional dimension that does not exceed about 1 mm, in other embodiments does not exceed about 500 µm, in other embodiments does not exceed about 300 µm, in yet other embodiments does not exceed about 100 µm, in other embodiments does not exceed about 50 µm, in other embodiments does not exceed 20 µm, in other embodiments does not exceed about 10 µm, in other embodiments does not exceed about 5 µm, and in yet other embodiments does not exceed about 1 µm). In situ assembly can enable the modification of flow channels within generic sealed sensors. Generic nanostructures can be assembled within flow channels then modified in situ to make them specific for a particular use such as for the detection of a particular target substance or pathogen. As illustrated in FIG. 2, this can be accomplished, for example, by attaching histidine-tagged Protein A or G 200 to NTA-Ni(II) 202 presenting colloids 204 within a nano-structure in a flow channel, and then flowing a sample through the channel that contains an antibody 206 presenting a binding partner to a particular target agent. The antibody will then bind to the Protein A or G 200, and thus make the nano-net specific for the capture of the target agent.

Most conventional sensors have a "dedicated" sensing capability; i.e. one sensor technology can detect target DNA, while another detects target proteins, etc. Methods provided according to certain embodiments of the invention can enable simultaneous detection of a variety of different target agents in parallel in array format. These target agents can include nucleic acids, peptides, proteins, whole cells, etc. In situ assembly or modification can allow for disassembly and reconfiguration of nano-nets within flow channels. Kits that contain separate inventories of pre-formed colloids and recognition elements, such as antibodies, for target agents can be pre-packaged for use with generic sensors, rendering the sensors readily customizable for a particular assay. Alternatively, pre-formed SAM-coated particles or colloids can be suspended in nano-nets already assembled into generic sealed sensors. To customize the nano-nets in situ, with identifiers (e.g., binding partners) of target analytes or pathogens, one need only inject into the sensor a pre-packaged solution containing the desired probe ligand, which can be modified or configured to bind to the colloids, which ligand can, for example, be an antibody.

Nanostructures provided according to the invention can be formed in and/or attached to channels constructed from a wide variety of materials, including, but not limited to, gold or gold-coated substrates, silicon, and poly vinyl chloride (PVC) or a wide variety of other other polymeric materials. The nanostructures can be attached to the channel surface via direct or indirect binding or coupling. In a preferred embodiment, the nanostructure is attached to a substrate that has been coated with a SAM bearing binding partners of moieties that are attached to the polymers and/or the colloids comprising the nanostructure.

In another aspect of the invention, nanostructures can be formed across multiple flow channels, within the same sensor, and differentially modified at different spatial locations to perform a variety of assays, in parallel, on a single sample. The ability to identify a suspect target by simultaneously analyzing multiple DNA, protein and cellular determinants can increase the accuracy and/or flexibility of detection by, for example, orders of magnitude. In a preferred embodiment, colloids located in different flow channels of a microsensor or other microfluidic network are derivatized with binding partners for specific DNA signatures, protein identifiers, and/or cellular or spore-specific markers, etc., to enable the identification of a particular target by simultaneously detecting several markers. Alternatively, each flow channel of a multi-channel sensor can be modified to perform the same assay on multiple samples, in parallel.

In some embodiments, the nanostructures can function as filters, which are useful for sample preparation, such nanostructures can exclude excess, irrelevant biological matter and any cell debris that could potentially interfere with bioassays. The effective pore size of the filter can be adjusted to exclude debris of different size ranges by varying: (1) the length of the interconnecting polymer chains; and (2) the size of the particles, with a size range between about 2 nm and about 200 nm diameter being generally preferred.

The nanostructures can also function as concentrators when the particles of the structures present a binding partner that binds to a target substance of a sample suspected of containing the target substance. In this way the sensitivity of detection devices can be improved by pre-concentrating the target analyte prior to release of the analyte, via an appropriate eluting agent or treatment (e.g. exposure to a chemical eluent, pH change, thermal change, etc.) for downstream determination/detection. This aspect of the invention can also be used to separate a target substance from irrelevant background materials. To concentrate a target substance, colloids or particles of the nanostructure can be derivatized with antibodies or other substance providing bidning partners for the target substance or pathogen as well as moieties to facilitate binding to the interconnecting polymer network (e.g., nucleic acid web). In some embodiments, the extent of concentration of an analyte by the nanostructure can be allowed to proceed to a point where fluid flow along a channel containing the nanostructure is essentially blocked (as described in more detail below) before releasing the analyte to permit fluid flow through the nanostructure and to permit downstream determination of the analyte.

Figure 3:
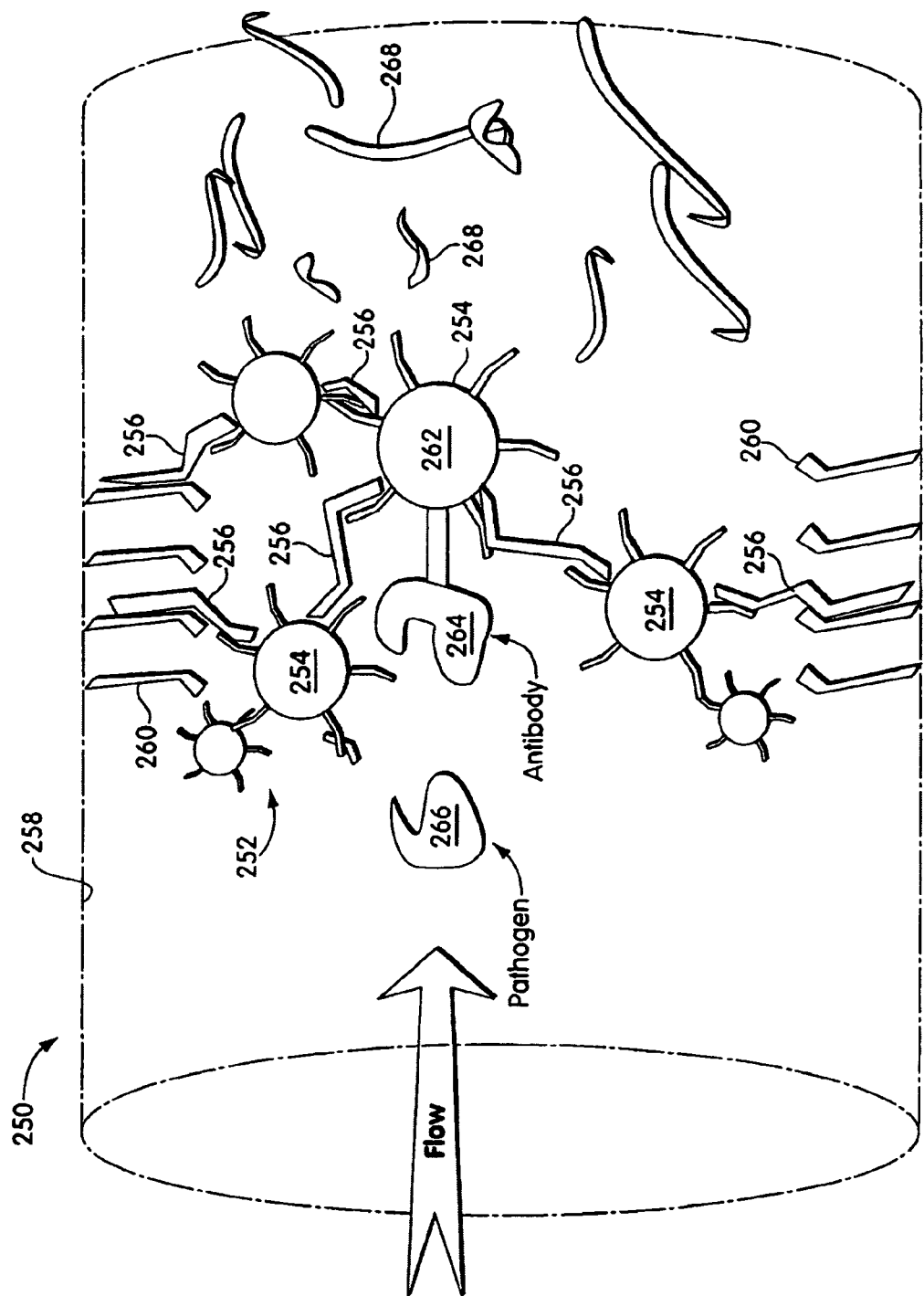
FIG. 3 is a schematic illustration that illustrates how nanostructures can used as biospecific concentrators when the embedded nanoparticles are derivatized to bear ligands that recognize a target agent.

FIG. 3 is a schematic illustration of a nanostructure configured as a biospecific concentrator. In the illustrated embodiment, flow channel 250 includes therein nanostructure 252 comprising colloids 254 interconnected to each other via polymer chains 256, thereby forming a nano-net. Nanostructure 252 is anchored to inner wall 258 of conduit 250 via binding interaction between polymers 256, fastened to colloids 254 and polymers 260, which are fastened to inner wall 258 of conduit 250. At least some of colloids 254 (e.g., colloid 262) further comprise, fastened thereto antibody molecules 264, which comprise a binding partner for a desired analyte to be concentrated, for example, pathogen 266, as illustrated. Upon passage of flow through channel 250, pathogens 266, which have affinity for antibodies 264, will tend to become bound to the nanostructure and immobilized, while other substances (e.g., 268) contained in the fluid stream can freely pass through the nanostructure.

Figure 4:
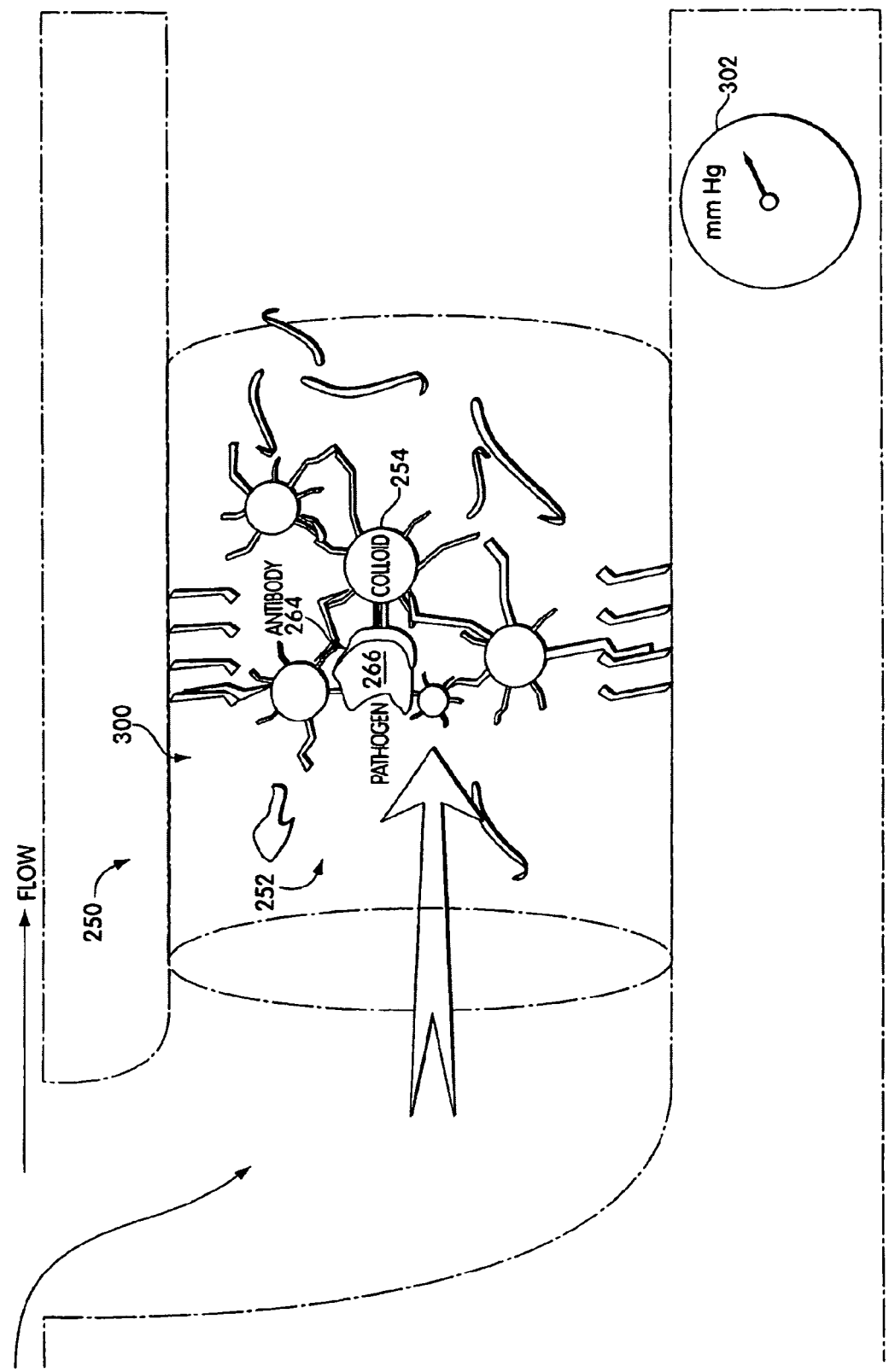
FIG. 4 is a schematic illustration that shows how the capture of a target agent in the nanostructure of FIG. 3 is sensed by detecting changes in flowrate or a change in the pressure gradient across the nanostructure.

The described nanostructures can, in some embodiments, also be used as in situ biosensors, one example of which is illustrated in FIG. 4 and described below. Such a biosensor 300 can be configured to operate as follows: when target substances 266 bind to recognition groups (e.g. antibodies 264) on colloids 254 or particles in the nanostructure 252, they become trapped and impede flow through the channel by altering its effective open cross-sectional area. The capture of a target substances in the nano-net can then be detected by detecting changes in flow rate, pressure and/or electro-osmotic forces across the filter, which result from the interruption of flow through the channel. Detection of a target by detecting changes in pressure drop, for example with differential pressure monitor 302, is a preferred embodiment because the pressure required to maintain a given rate of flow through a channel is inversely proportional to the fourth power of the effective diameter of the open area channel, making this approach very sensitive.

The nano-sensor, described above, can provide, in preferred embodiments, remote, real-time, continuous monitoring of a fluid medium with very low power consumption. As one example, a water supply could be continuously monitored for the presence of multiple target contaminants or pathogens. The interaction of the particle-presented ligand with the target tends to clog the nano-net and interrupt flow, which, as described above, can be detected with a high level of sensitivity. The sensor could, if desired, be electrically or electronically integrated into a feed-back loop such that a measured change in either the flow rate or pressure drop would result in the triggering of a stop-flow mechanism to shut down distribution of the contaminated water.

One aspect of the invention provides for a modular system is which generic nanostructures are pre-formed in flow channels, then customized at a later time to present ligands or binding partners that recognize a target substance. The recognition ligands can include antibodies, proteins, peptides, DNA and/or synthetic molecules, etc., that comprise binding partners specific for a target substance.

Figure 6:
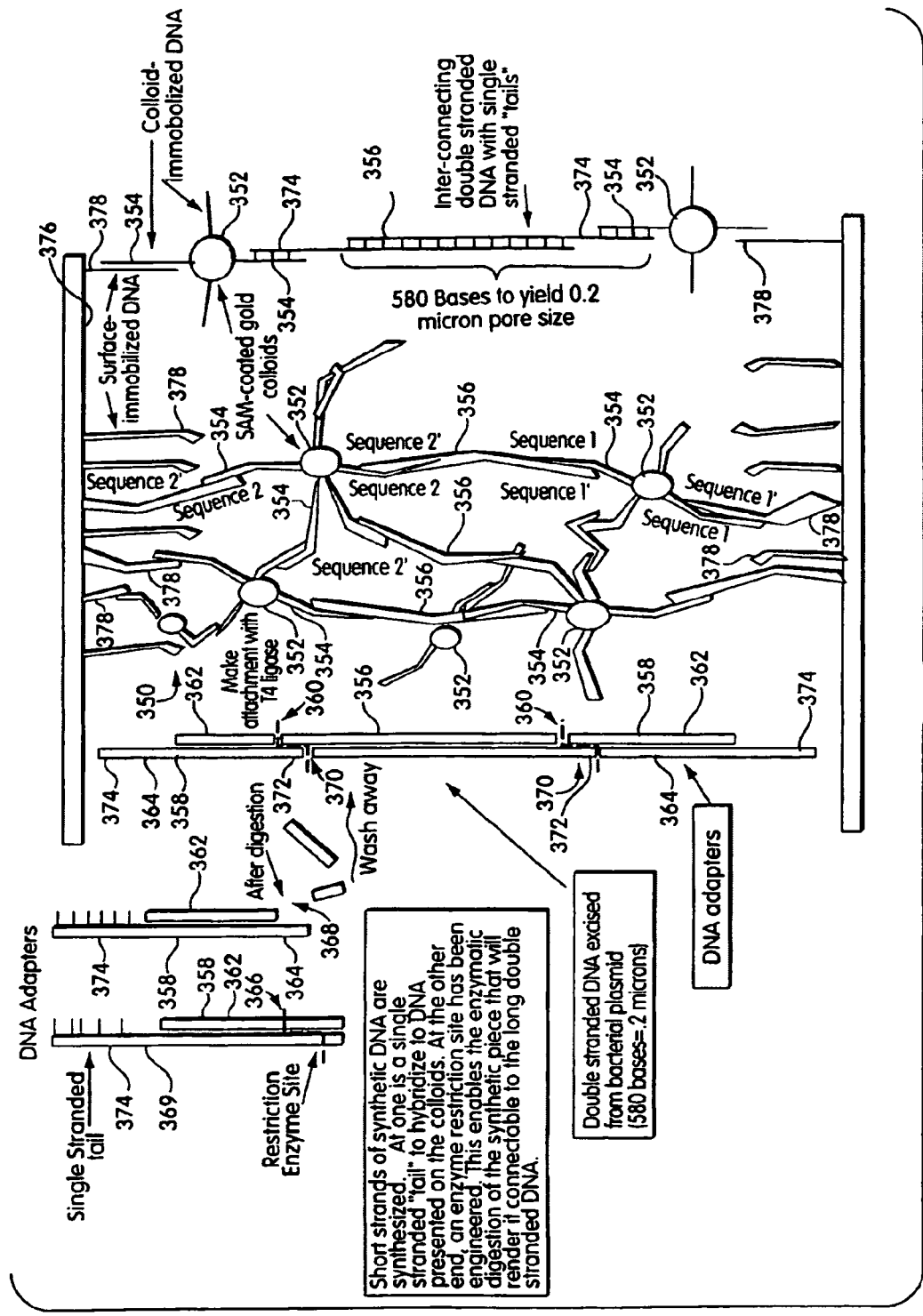
FIG. 6 is a schematic illustration showing a scheme for constructing nano-structures from DNA-derivatized colloids and DNA modified with adapter sequences to facilitate the formation of a particle-polymer network.

In some embodiments, the nano-net can be formed by connecting colloids with strands of DNA (e.g. as illustrated in FIG. 6 and described below). This can be accomplished, for example, by derivatizing colloids with SAMs that present: (1) a moiety that binds to a group attached to or contained within the DNA; (2) a recognition ligand/binding partner that binds to a target substance; and preferably, and, preferably, (3) moieties that render the colloid resistant to non-specific binding. For example, colloids that are derivatized with SAMs that present DNA, nitrilo tri-acetic acid chelating nickel (II) (NTA-Ni(II)) and ethylene glycol groups can self-assemble into 3-dimensional structures when the DNA presented on the colloid is complementary to the end fragments of strands of spanning DNA. The NTA-Ni(II) groups can capture histidine-tagged proteins that recognize the target substance and present the proteins for binding to the target substance. Ethylene glycol head groups help the colloid resist non-specific binding. Any one of a number of histidine-tagged or other metal binding tagged recognition ligands can potentially be attached to the colloids to alter the specificity of the nano-net. Recognition ligands can be attached to the colloid before or after the assembly of the nano-structure. To customize a nano-net, including colloids that are derivatized with SAMs that present DNA, NTA-Ni(II) and ethylene glycol groups, that has been pre-formed across a flow channel with binding partners of a particular target substances (i.e., "recognition elements"), a solution containing a histidine-tagged recognition element can simply be flowed through the nano-structure. Alternatively, a histidine-tagged fragment of Protein G, which binds to the Fc portion of antibodies, can be attached to colloids that bear NTA-Ni(II). In this way, essentially any antibody can be readily attached to the nanostructure, to capture a wide variety of targeted substance.

In other embodiments, probe ligands can be attached to the colloids or particles by methods other than NTA-Ni(II)—histidine-tag binding. For example, other binding partners of affinity tags can be attached to the colloids to capture and present affinity tag-labeled recognition elements. For example, glutathione can be attached to the colloids, which can bind glutathione-S-transferase (GST) fusion proteins. In a preferred embodiment, the glutathione is covalently fastened to a thiol, which is then incorporated into a self-assembled monolayer that is formed on a gold colloid. Alternatively, recognition elements can be covalently fastened directly to colloids or particles. For example, colloids that bear exposed carboxy groups can be coupled via EDC/NHS chemistry to primary amines in the ligand comprising the recognition element.

One advantage of attaching a recognition element to the colloid via an affinity tag interaction with a group on the colloid is that the captured target can then be conveniently released from the nano-net for downstream detection. For example, a captured target substance that is bound to a histidine-tagged recognition element, immobilized on a particle, can be released by the addition of imidazole, which competes for binding to NTA-Ni (II) with the histidine tag. The amount of imidazole that is required for the release is dependent on the amount of NTA-Ni(II) present on the surface and therefore is a constant, which is independent of the concentration of the captured target substance. Conversely, if the target substance is captured by groups that are covalently fastened to the surface of a particle, then the conditions, such as changes in pH and the like, necessary to release the target are dependent on the amount of target that was captured, which often cannot be known a priori.

Figure 5A:
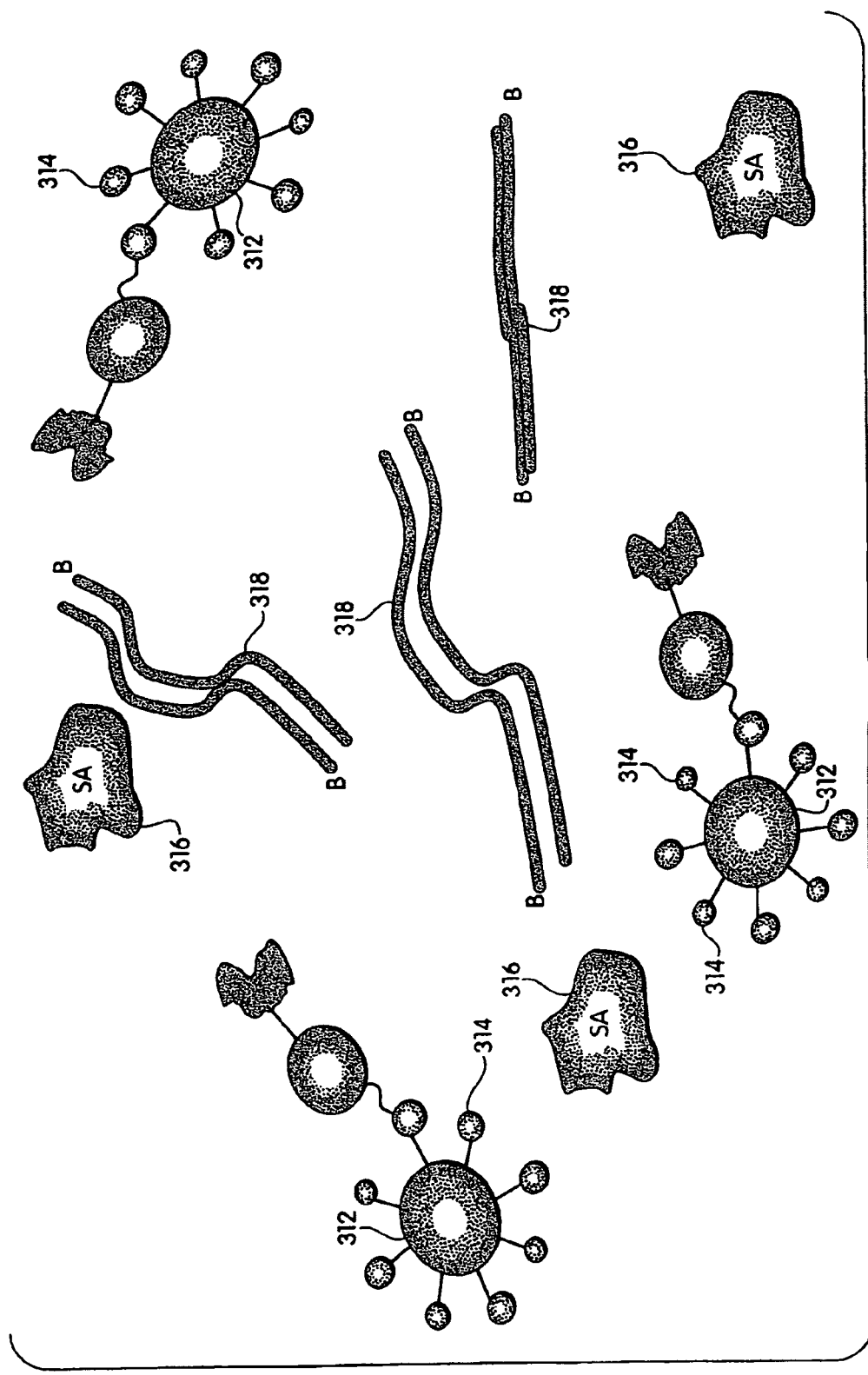
FIGS. 5A and 5B are before and after schematic illustrations illustrating how nanoparticles bearing antibodies and biotin interact with streptavidin and biotinylated dsDNA to form nanostructures that are biospecific.
Figure 5B:
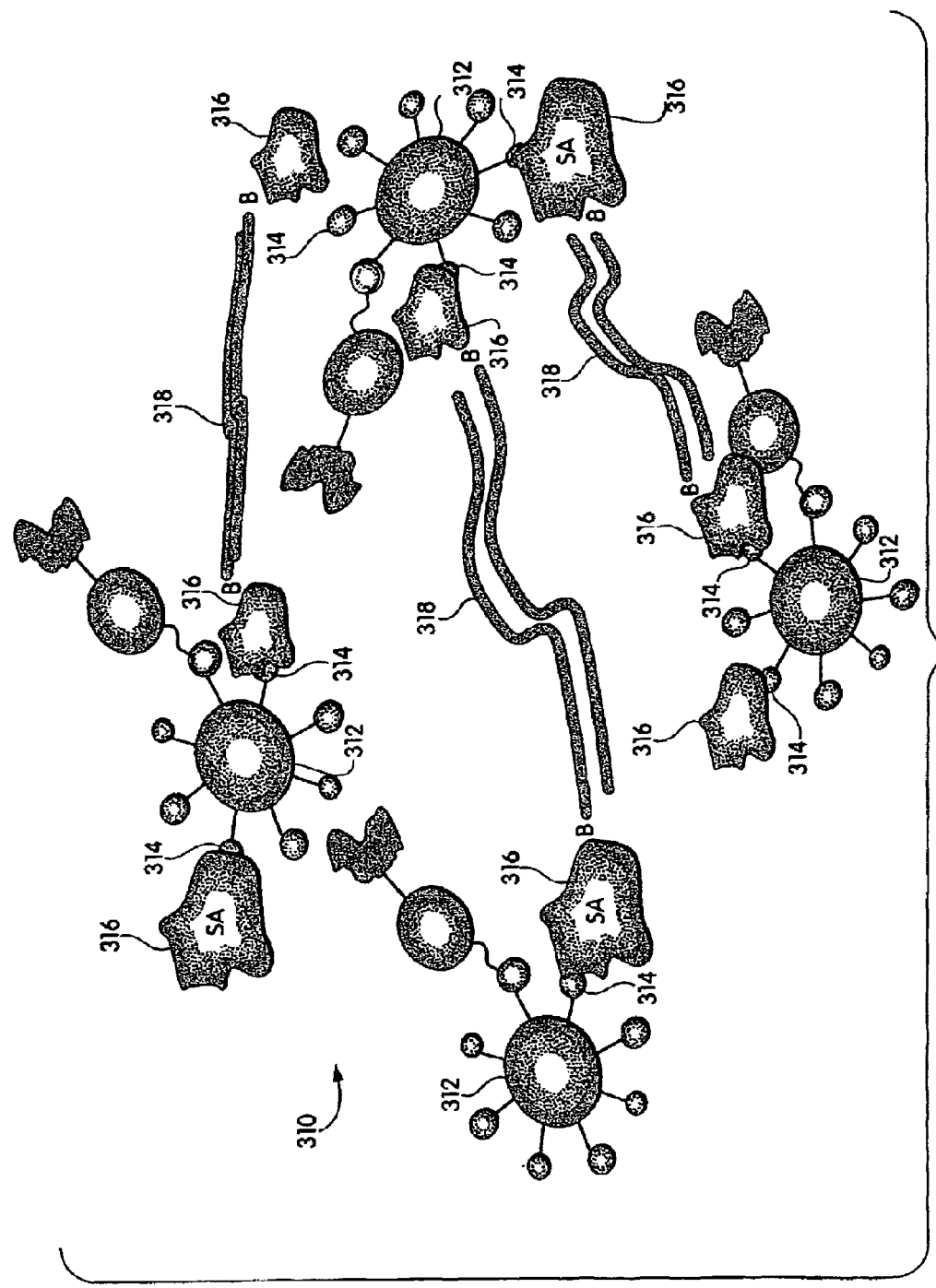

Three-dimensional structures constructed of particles and connecting polymers can be constructed across flow channels using a variety of alternative methods to that described above. For example, as illustrated in FIGS. 5A and 5B (which illustrate the various components comprising the nanostructure before (FIG. 5A) and after (FIG. 5B) the self-assembly of the interconnected structure) nanoparticle-DNA nanostructures 310 can also be self-assembled by mixing nanoparticles 312, bearing biotin 314, with streptavidin 316 and DNA 318 that has been modified at or near its ends with biotin (B). Long strands of biotin-modified DNA can be generated by conventional PCR techniques using biotinylated primers. Alternatively (not shown), colloids modified with strepavidin can be bound to attached directly to biotin-modified DNA. This type of nanostructure can readily be attached to flow channels bearing streptavidin at its surface. Streptavidin can either be directly attached to the channel surface or can be attached indirectly via binding to biotin groups on the surface. In one preferred embodiment of the above-described indirect linkage, SAMs that present biotin are formed on one or more surfaces of etched or machined channels that have been gold-coated.

As illustrated in FIG. 6, colloid-DNA nanostructures 350 can also be formed by derivatizing colloids 352 with a short strand of DNA 354 that is complementary to an end of a longer, linker strand of DNA 356. Although it is straightforward to connect colloids via synthetic DNA oligos that are complementary to DNA presented on the colloid surface, such synthetic pieces of DNA are less preferred for forming the structural elements of the nano-nets provided according to the invention. DNA oligos typically cannot, using presently available techniques, be synthesized above a maximum length of about 70 base pairs. Such length would correspond to a spanning length of only about 24 nm, while the diameter of a typical colloid can be, for example, on the order of about 10-30 nm. Such short strands are not long enough to provide the degree of open area and effective pore size preferred for nano-nets provided by the invention. Thus, in preferred embodiments, longer strands of DNA 356 (tens to hundreds to thousands of base pairs or more) are enzymatically cut out of bacterial plasmids. These pieces of DNA are double stranded and therefore the nucleotides are unavailable to hybridize to the short strands of DNA 354 presented on the colloid surfaces. Accordingly, to facilitate attachment of these pieces of double stranded DNA to colloids or particles, short DNA "adapters" 358 are enzymatically ligated onto each end of the long double stranded DNA (e.g. at 360). These adapters can be constructed from two pieces of synthetic DNA 362, 364 that are complementary over at least a portion of their length but are of different lengths. The adapters 358 can be enzymatically cut at an enzyme restriction site 366 engineered into the adapter at one end to connect, after digestion 368 with a suitable enzyme, to the double stranded DNA which has been similarly digested at its ends 370 with an enzyme to cleave off a fragment of a single-stranded DNA to expose a short single stranded length 372 for hybridization with the adapters 358 (the restriction enzyme sites in the plasmid DNA can easily be chosen using known techniques such that the excised strands are of uniform length). The other end 374 of adapters 358 presents a single stranded "tail" for hybridizing to the colloids 352. This type of structure can be attached to a flow channel 376 via DNA hybridization to surface-immobilized DNA oligonucleotides 378. Alternatively, the flow channel can be derivatized with a group that recognizes a binding partner on a first set of colloids or a first set of polymer chains. This first set of colloids or polymers can be designed such that it connects the channel surface to the nanostructure, while subsequent particles and polymers link to each other. The above-discussed DNA modification techniques are well understood by those skilled in the art.

There are two basic strategies for the in situ construction of nanoparticle-polymer nano-nets. One is spontaneous self-assembly while the other is a step-wise self-assembly. For example, in the former method, DNA-presenting colloids and interconnecting DNA are mixed together in bulk in the proper proportions resulting in the spontaneous formation of an essentially complete, spatially localized nano-net spanning a flow channel. The later strategy, by contrast, involves step-wise introduction of sub-portions of colloids then DNA elements (or vice versa) to build up the nano-net into an ordered assembly in a step-wise fashion.

Aspects of the invention also exploit the 3-dimensional nature of the nanostructures provided by the invention. Those skilled in the art of molecular biology realize that two or more antibodies are able to simultaneously bind to a target substance by recognizing two different epitopes on the target. The immobilization of two or more types of antibodies, recognizing different target epitopes, on separate colloid populations tends to cause the nanostructure to cross-link and condense along the length of the flow channel, as target substances or pathogens induce the aggregation of the colloids into a tight reticulum that reduces and, eventually, can virtually eliminate fluid flow. Alternatively, or in addition, a second colloid population, bearing a second antibody specific to the target and a signaling entity, can be introduced after the capture of the target substance or pathogen to render the target detectable either in situ or at a downstream sensing element via the signaling element.

Substrates, for example flow channel surfaces, can be modified to allow for the attachment of three-dimensional particle-polymer nanostructures in a variety of ways. In a preferred method, the surface of a flow channel is gold-coated and SAMs presenting a ligand to facilitate attachment of the 3-D structure are formed thereon. Alternatively, substrates including, but not limited to, PVC and PDMS can be modified according to the synthetic schemes described below to become covalently fastened or coupled to such ligands. A variety of techniques can be used to spatially confine the nanostructure within only a portion of the length and/or cross sectional area of the flow channel. These include, but are not limited to, techniques to confine a solution containing reactants to one region of the flow channel surface, techniques to introduce reactants to all of the surface but only activate a spatially distinct region, and techniques using microstamping technology to apply chemically functional groups or monolayer components onto a spatially defined region of the flow channel. Assembled three-dimensional nanostructures can be disassembled in situ by, for example, introducing heat, a heated solution, altered pH solutions, or chemical solutions, such as formamide, into the flow channel to disrupt the binding interactions supporting the structure.

Figure 7A:
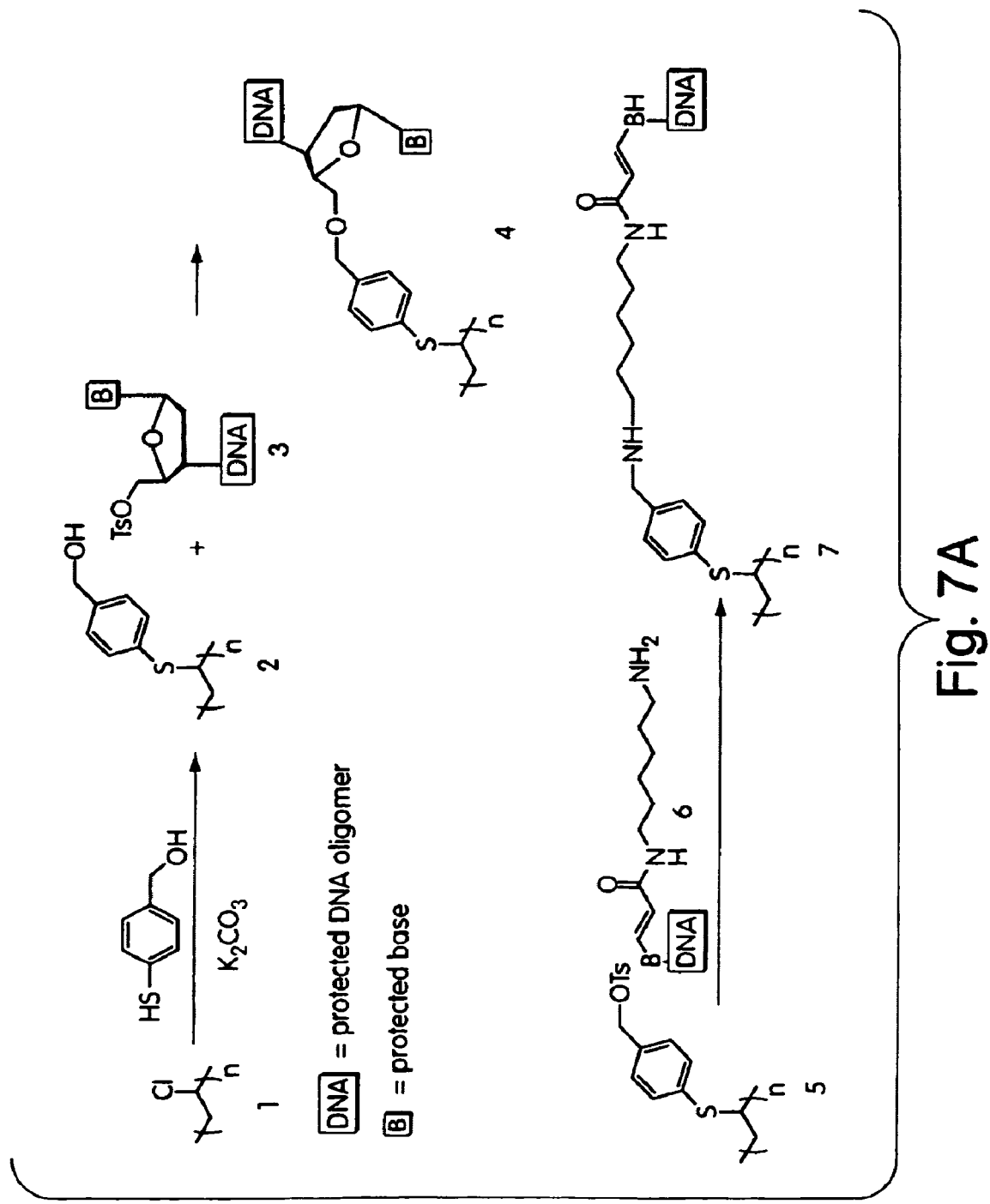
FIG. 7A is a schematic illustration showing a synthetic scheme for attaching DNA to a surface such as polyvinyl chloride.

As mentioned above, flow channel substrates can be comprised of a variety of synthetic polymeric materials, for example, polyvinyl chloride (PVC), polydimethylsiloxane (PDMS), polyvinyl alcohol, carboxylated PVC, and polyallyl amine, each of which can be readily coupled to DNA, biotin, or protein moieties that facilitate attachment of the nanostructure to the channel. For example, the attachment of a DNA fragment onto a PVC surface is illustrated in Scheme 1 shown in FIG. 7A, and described in detail in: Grafting on polyvinylchloride in suspension using phase transfer catalysts on solvents. Nkansah, A., Levin, G.; in *Modification of polymers* Eds.: Carraher, C. E., Moore, J. A., Plenum, New York, 1983, p. 109; PVC modification with bifunctional thiol compounds. Reinecke, H., Mijangos, C.; *Polymer Bull.* 36, 1996, 13; Synthesis of adjustable poly(vinyl chloride) networks. Reinecke, H., Hidanlgo, M. Mijangos, C.; *Macrom. Polymer Commun.* 17, 1996, 15; Migration resistant, blood-compatible plasticized polyvinyl chloride for medical and related applications. Lakshmni, S., Jayakrishnan, A.; *Artif Organs* 22(3), 1998, 222. The above strategy can be readily extended to facilitate the attachment of other recognition groups to this and other substrates. The nucleophilic displacement of the secondary alkyl chloride (1) with p-(hydroxymethyl)thiophenol selectively leads to the thioether (2). This process has been demonstrated to proceed cleanly and selectively in solution and in melt (se, for example, Effect of solvent on glass transition temperature in chemically modified polyvinyl chloride (PVC). Lopez, D. Mijangos, C., *Colloid Polym. Sci.* 272, 1994, 159). The degree of substitution, which is directly related to the density of the thioether groups on the polymer surface, depends on the experimental conditions, and is adjustable. The benzylic hydroxy group in (2), which does not react with PVC under the conditions of the formation of (2), is now used to attach an appropriately protected DNA oligomer (3). Several attachment protocols are available. For example, nucleophilic displacement of the 5'-sulfonate ester of (3) would furnish the coupled product (4) (For examples of similar displacement reactions see: A novel synthesis of 3'-deoxy-3'-nitrothymidine via nucleophilic substitution with nitrite anion. Huang, J. J., Ragouzeos, A., Rideout, J. L.; *J. Heterocyclic Chem.* 32, 1995, 691; and Synthesis of novel bicyclo[2,2,1] ribonucleosides: 2'-amino- and 2'-thio-LNA monomeric nucleosides. Singh, S. K., Kumar, R., Wengel, J.; *J Org. Chem.* 63, 1998, 6078). An alternative strategy would involve the nucleophilic displacement of the benzylic sulfonate ester of (5) with an amine of the DNA fragment, as in (6), to produce (7). Several 5'-amino modifiers that can be utilized to prepare compounds such as (6), are commercially available for use with standard DNA synthesis techniques (e.g. from Glen Research, Sterling, Va., USA).

Figure 7B:
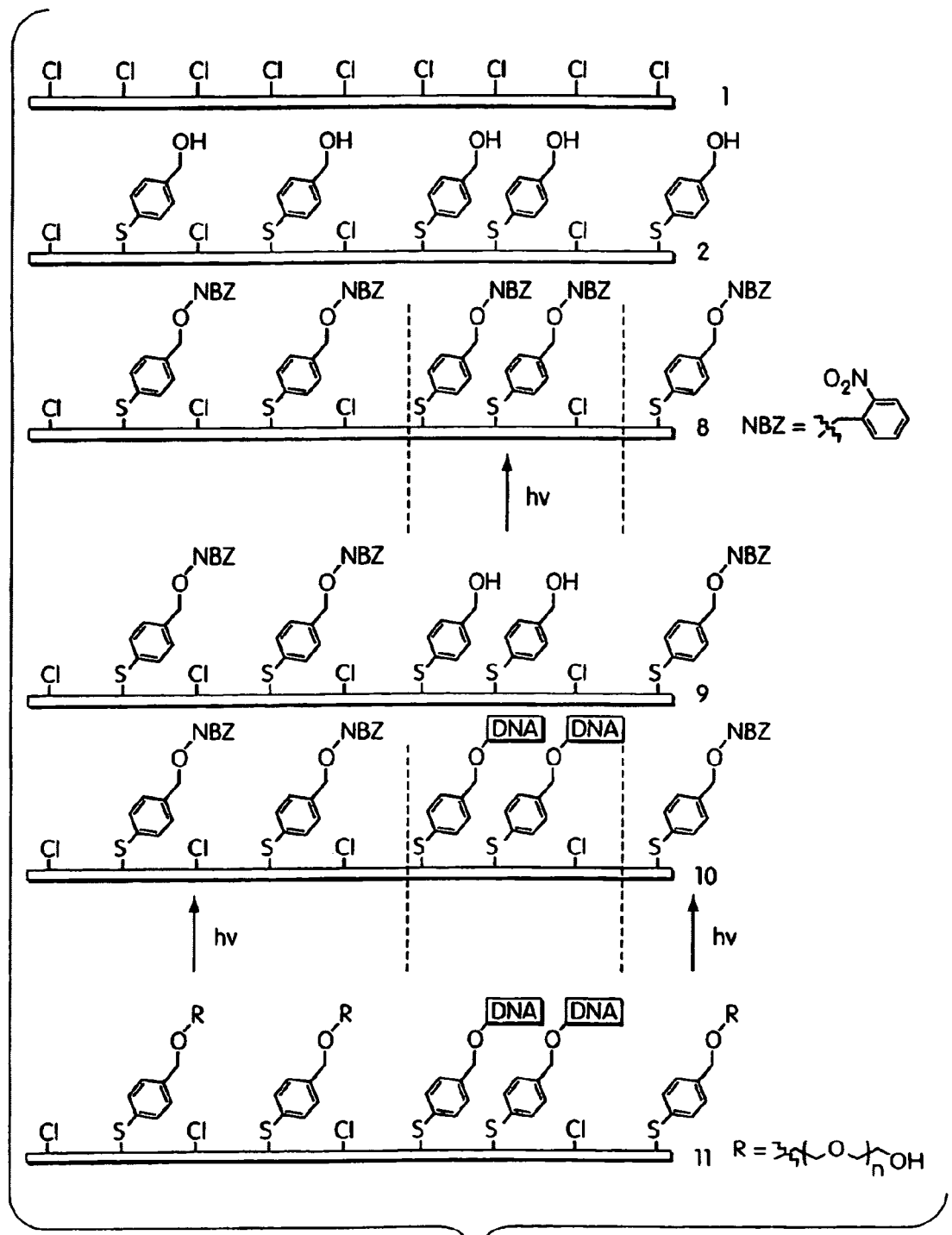
FIG. 7B is a schematic illustration showing a synthetic scheme for rendering a surface chemically functional in a spatially defined area for the attachment of a nanostructure across a thin region of a flow channel.

One process of polymer surface preparation for attaching a ligand for binding the nanostructure in selected spatial locations of the surface, while rendering the remainder of the surface substantially inert to non-specific binding, is schematically represented in Scheme 2 illustrated in FIG. 7B. The polymer surface (1) is modified with p-(hydroxymethyl) thiophenol to produce (2), as discussed above. The hydroxy groups that extend off the surface are now protected with a photolabile protecting group, such as 2-nitrobenzyl (NBZ), to obtain (8) (for a more detailed description of the technique see: *Protective groups in organic synthesis.* Greene, T. W., Wuts, P. G. M., Wiley, New York, 1999; and Photoremovable protecting groups in organic synthesis. Pillai, V. N. R.; *Synthesis,* 1980, 1). A small region of the polymer surface is selectively deprotected by irradiating with light (hv) of appropriate wavelength through a mask; this process liberates the surface hydroxy groups only in the specified area producing surface (9) (For references on light-directed spatially addressable chemical synthesis see: The efficiency of light-directed syntesis of DNA arrays on glass substrates. McGall, G. H., Barone, A. D., Diggelmann, M., Fodor, S. P. A., Gentalen, E., Ngo, N.; *J Am. Chem. Soc.* 119, 1997, 5081; and Light-directed, spatially addressable parallel chemical synthesis. Fodor, S. P. A., Read, J. L., Pirrnung, M. C., Stryer, L., Lu, A.T., Solas, D.; *Science,* 251, 1991, 767). The free hydroxy groups are now used to attach the DNA fragments as described above to prepare (10). Finally, the rest of the surface is deprotected and the available hydroxy groups are employed to attach ethyleneglycol oligomers to form (11).

In another preferred embodiment flow channels are formed with multiple detection locations along the flow paths. A preferred approach is to mix the sample with several species of signaling colloids that present a variety of recognition elements that are specific for a variety of targets. Recognition elements can be nucleic acids, proteins, small molecules, prion-like peptides, antibodies, or small molecules that interact with target molecules (including, for example, fibrils, protofibrils or ordered peptide aggregates). The sample and colloid mixture, called the sample plug, is sent through flow channels to discrete, spatially addressable locations that also house a second recognition element that is specific for one of the suspected targets.

Figure 8A:
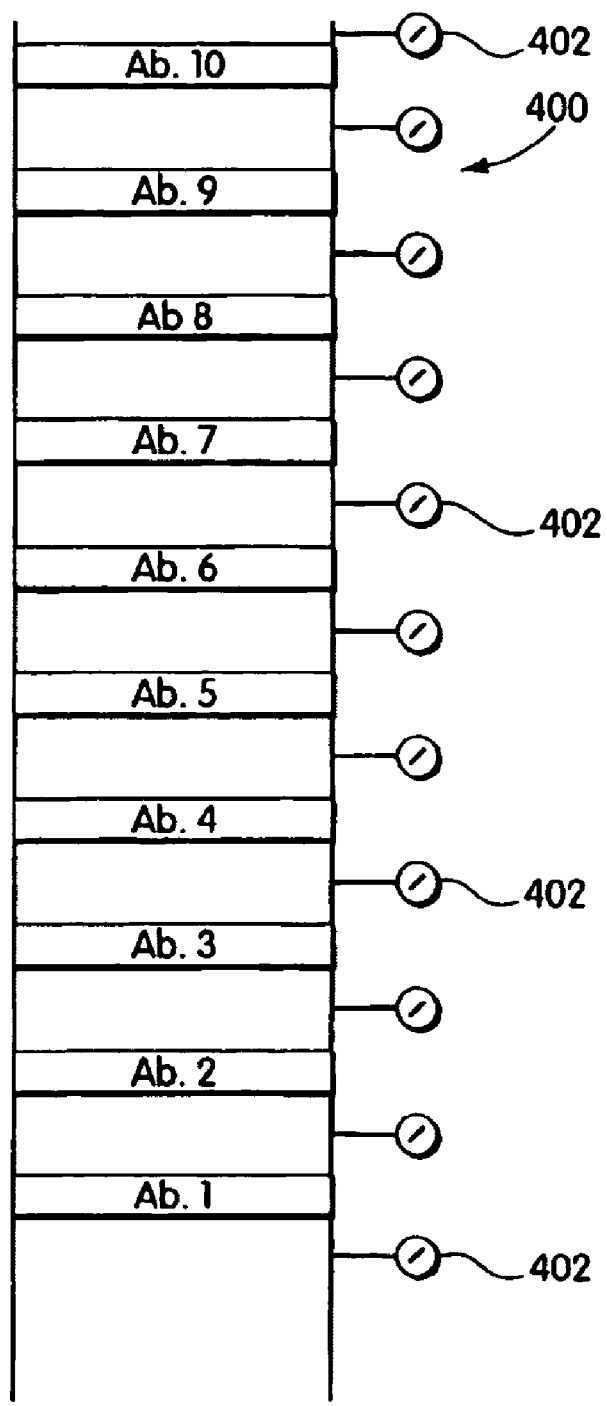
FIG. 8A is a schematic illustration of a multi-target biosensor according to one embodiment of the invention.
Figure 8B:
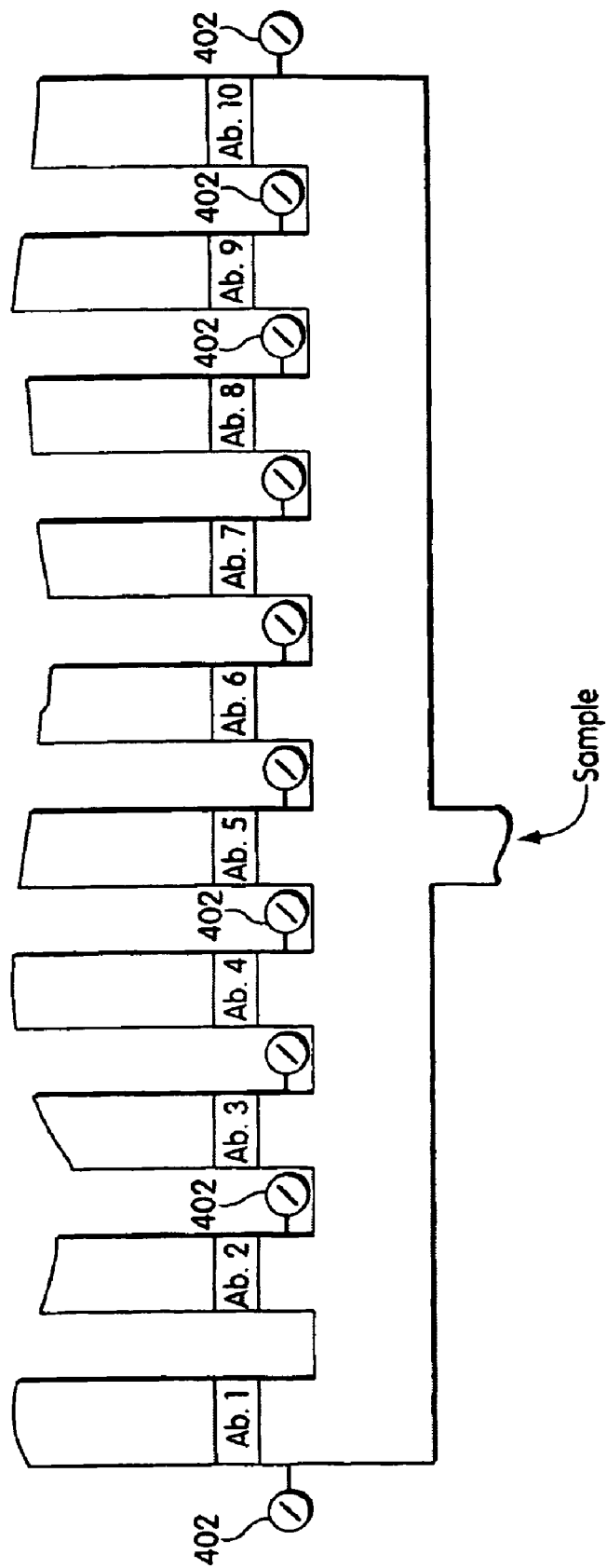
FIG. 8B is a schematic illustration of a multi-target biosensor according to another embodiment of the invention.

For example a first embodiment of a multiple detection location flow channel system is illustrated in FIG. 8A. As illustrated, a series of probe ligands comprising antibodies, denoted Ab 1-10, can each be immobilized directly to the channel surface or included in a separate nano-net surface immobilized in discrete locations along a single flow path 400. A sensing element, such as a pressure sensor or flow rate detector, etc. 402, is positioned adjacent each discrete region that presents a probe ligand. A sample, suspected of containing a target agent, is mixed with a set of nanoparticles that each present an antibody, denoted Ab A-J. In this system, Ab 1 and Ab A each recognize different epitopes on a first specific target pathogen, as do Ab 2 and Ab B for a second target, Ab3 and Ab C for a third target etc. In this way, the analysis of pressure drop profile through a specific channel 400, at a specified locations, can identify which of a variety of target agents is present in the channel and, thus, in the sample. Alternatively, instead of the discrete regions presenting Ab. 1-10 being located along the length of a single flow channel, each of Ab 1-10 could be immobilized in a separate flow channel, as illustrated in FIG. 8B, with the sample, mixed with a set of nanoparticles that each present an antibody, denoted Ab A-J, being flowed alond each flow path. The analysis of pressure or flow rate along each flow path can identify which of a variety of target agents is present in the sample.

Figure 9:
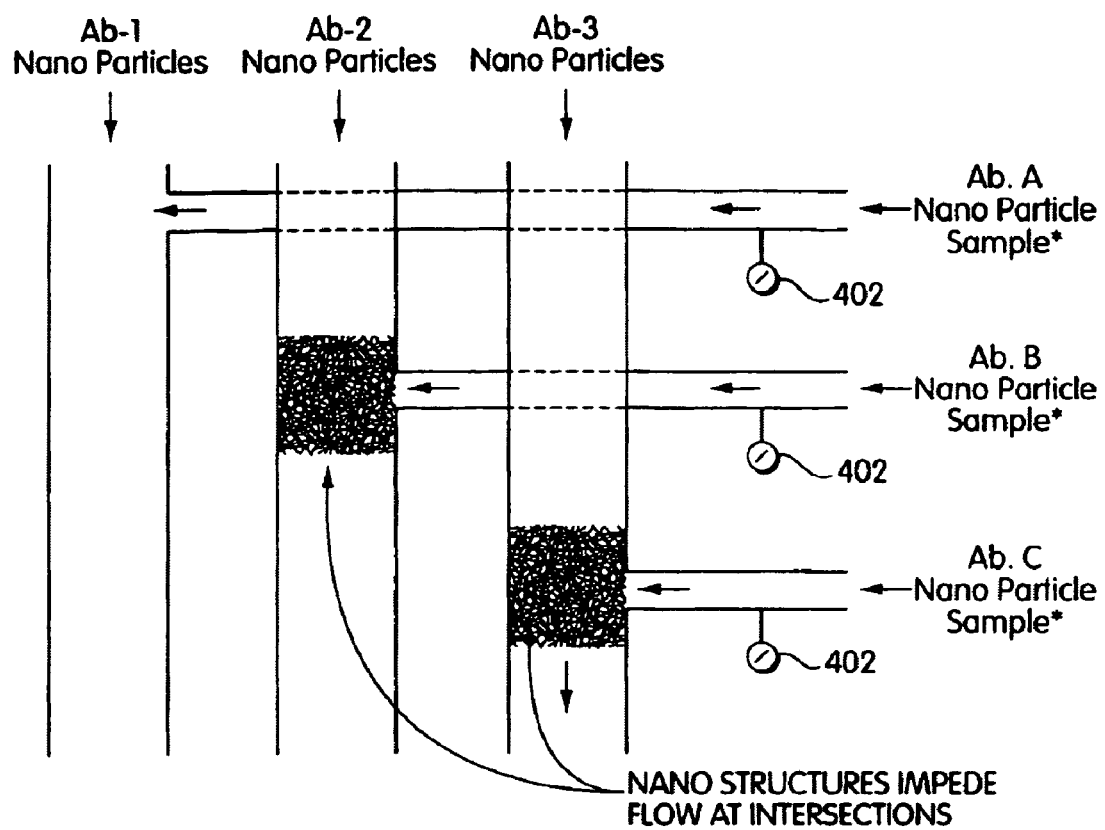
FIG. 9 is a schematic illustration of a multi-target biosensor according to yet another embodiment of the invention.

Alternatively, as shown in FIG. 9, both of the above sets of antibodies can be presented on nanoparticles in free solution.

In the illustrated embodiment, each of Abs 1-10-containing nanoparticles (only Ab 1-3 channels are illustrated for clarity) are directed to separate flow channels in which flow proceeds in a first direction. Aliquots of a sample are separately mixed with Abs A-J and each is directed to separate flow channels (only Ab A-C channels are illustrated for clarity) that are orthogonal to the first set of channels. In this way, flow is impaired at the intersection of the flow path of Ab 2/Ab B and Ab 3/Ab C which simultaneously recognize target agents in the sample and form a cross linked nanostructure.

Another approach is to sequentially direct the sample to locations that house recognition elements specific for one target and based on the detected presence or absence of that target, the sample can be re-directed to a subsequent location based on a logical algorithm. Alternatively, the sample can be simultaneously introduced to all the locations and the querying of the locations is performed according to a logical algorithm, based on detection results at decision points. Alternatively, the presence of the target species is interpreted by a logical algorithm. The presence of a particular aspect, characteristic or epitope of the target agent can be detected at one location, and based on this detection the sample plug is re-directed to the next location where a different aspect, characteristic or epitope of the target agent can be detected. In this way, a logical diagnostic test can be performed.

Logical diagnostic test systems, according to the invention, can be implemented in a variety of ways, for example, the original sample plug can be introduced into a mixing chamber where it is mixed with signaling particles that bear recognition elements specific for many targets. In another preferred embodiment, the flow through flow paths of the system can be interrupted by the binding of target substances. In such a case, detection can be made by pressure measurements, and, in some embodiments, flow diversions to particular flow paths can be accomplished by such flow path interruptions. This method can include immobilizing a binding partner within a section of the flow path to enable impeding of the flow. The impeding of the flow results in a higher pressure drop across the impediment and/or in a reduced flow rate. In each case, the change can be detected and used to make quantitative and qualitative determinations. The sample and particle mixture are directed through a maze of flow channels that at discrete sensing locations display a local recognition element. These localized recognition elements can be configured to form a set that is complementary to the set of recognition elements that are particle-immobilized in that one element from each set can simultaneously bind to a particular target agent and thus interrupt the flow channel if such target agent is present in the sample. The results of each measurement at each sensing location can be used by a controller to activate a small fluid valve, herein referred to as a micro valve, to re-direct flow through the connecting channel to the next measuring chamber. Depending on these measurement results the flow may be directed to other chambers, etc. Note that each chamber is simply a convenient flow path and does not participate in the assay itself, however, each chamber provides a measurement capacity, for example of pressure, flow rate, etc.

Figure 10:
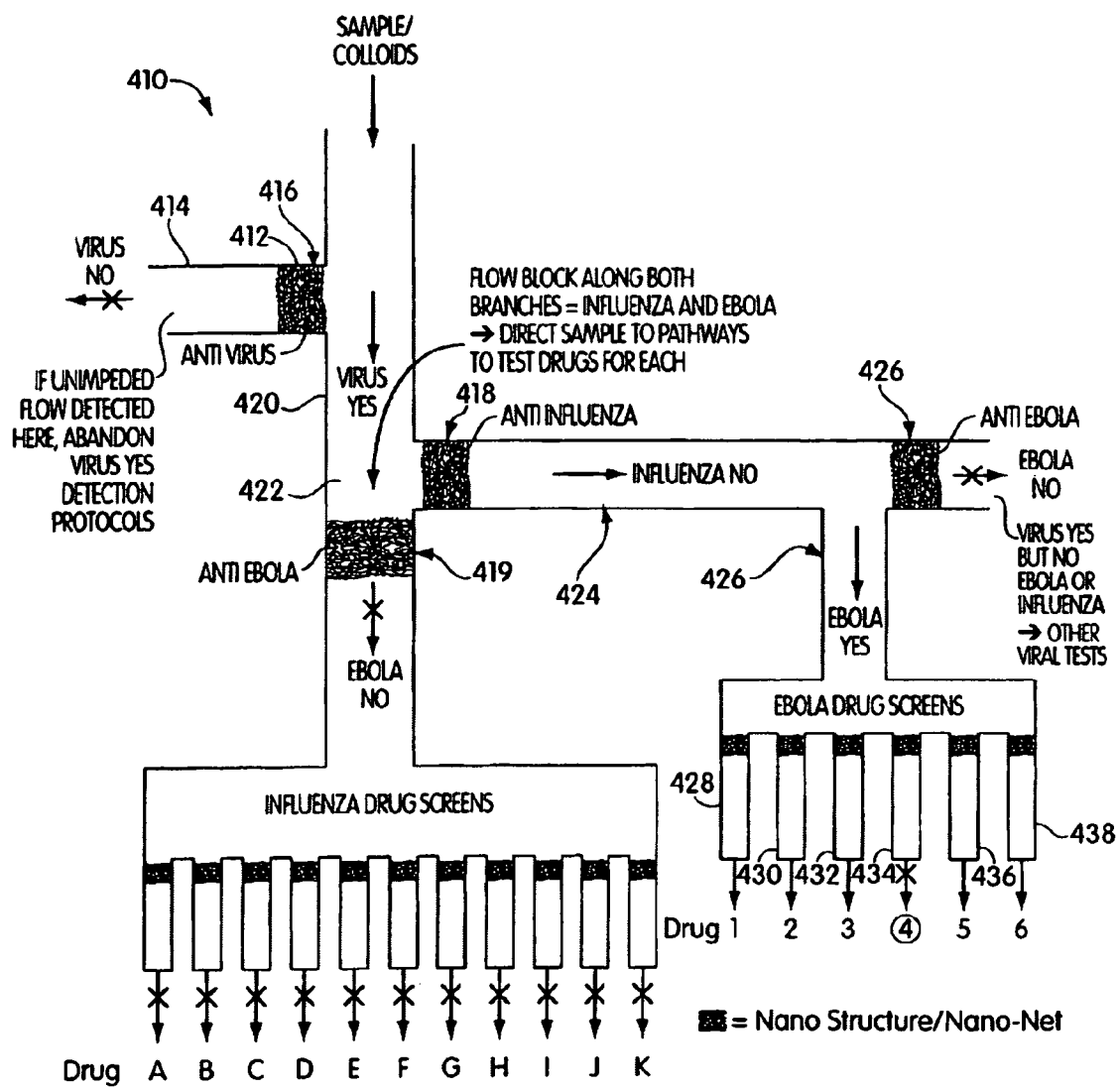
FIG. 10 is a schematic illustration of an automatic switching biosensor for logical processing applications according to one embodiment of the invention.

In an especially preferred embodiment, as illustrated in FIG. 10, the sample, optionally also containing target-specific nanoparticles, is allowed to direct its own path through the maze of flow channels 410. When an agent, present in the sample, simultaneously binds to a recognition element on a particle (when present) and/or a recognition element(s) at a discrete spot 412 along a flow path 414, a nano-net 416 forms that acts as a valve to blocks flow through that portion of the channel network. The path that the sample followed through the flow channel network is then analyzed to determine which target agents or aspects of a target agent were present in the sample. An example of logical flow operation of the microflow techniques described above illustrated in FIG. 10, involves forming a sample mixture of containing the sample and many biospecific colloids that present ligands that are specific for certain target molecules. Then sequentially flow the sample mixture through locations that each house a second ligand that is also specific for one of the target molecules. For example, a first location 412 along a flow path may ask the question "Is it viral?" (i.e. a nanostructure 416 includes antiviral ligands) whereupon, if virus is present and binding of sample/colloid occurs, flow is directed to a second location by the plugging or formation of a nanonet and the blockage of flow; in this case the recognition event acts as an activatable micro valve. The next locations 418, 419 may ask, "does the virus have homology to influenza?" or "Does it have homology to Ebola?" If yes then the sample is directed to a location that asks, "What is its drug resistance?" and the like. In the example illustrated in FIG. 10. The sample plug reacts forming a plugged nano-net at locations 412 (yielding no floe through channel 414="virus yes). Flow is then diverted along "virus yes" channel 420 to branch point 422. The sample plugs the anti-Ebola nanostructure at location 419 but passes freely through location 418 containing an anti-influenza nanostructure, thus indicating that the sample contains Ebola but not influenza. The sample continues along channel 424 to branch location 426, which contains an anti-Ebola nanostructure, which becomes blocked, thus diverting flow to the Ebola drug screens along channel 426. The flow then proceeds to channels 428, 430, 432, 434, 436, and 438, each of which contains a nanostructure presenting a drug candidate whose affinity to Ebola is under investigation. Channels that become plugged correspond to drug candidates with affinity to the Ebola target, with the degree of plugging being correlated to the degree/affinity of interaction. As illustrated, the sample is Ebola positive/influenza negative, and drug candidate 4 has affinity for the Ebola.

Alternatively, a small portion of the sample could be delivered to a discrete sensing location, while the major portion of the sample would be retained in a sample chamber of a robotic sample delivery arm. Based on the detected presence or absence of a target substance in the first location, the robotic arm would be directed (based on a logical algorithm) to deliver a subsequent aliquot of the sample to a second sensing location. In this way, logical diagnosis and logical sensing can be accomplished with a minimum of microfluidic engineering.

Detection by the interruption of flow can be especially useful in situations where constant monitoring is required, as in plants where food, water, and/or drinkable fluids are being processed. An advantage of such flow monitoring is that little or no energy is required. The plant is causing the material to flow as part of the process itself, so that tapping off a small portion of the flow or placing the measuring locations along the main flow allows the processing flow pressure to move the sample entails little or no additional energy input. When or if a problem is found automatic valves can be activated to shut down the processing line until the problem is corrected. The activation energy for the shutdown valve can also come from the plant's processing flow pressure. The detection of problem substances can be made by flow detection or by any of the other above-described methods where the choice is determined by the specific parameters and needs of the process being monitored. In such instances a stable, robust ligand is preferred. Where flow interruption is a desired detection scheme, the target and the ligand can be designed to create 3-dimensional structures comprising polymers, which are strong and long so as to efficiently interrupt flow. Alternatively, a polymer bearing two elements that simultaneously recognize different regions of a common target could be used to form molecular meshes that could efficiently reduce flow. Preferred ligands comprise a complementary nucleic acid, a protein or peptide, a protein complex, or an antibody that is a binding partner, a small molecule or a synthetic recognition element.

Flow interruption can also be generally used to intentionally block flow and replace the essentially any "nanovalve" in a micro- or nano-fluidic system In preferred embodiments the flow blockage mechanism can be designed to be reversible so that the system is reusable. For example, DNA oligos can be immobilized on the interior of a flow channel that also houses beads/particles/colloids with DNA oligos. Bridging oligos can simultaneously bind to both surface ligand and bead ligand to form a molecular mesh, as previously described. Moreover, the length and sequence of the bridging oligos can be designed to form molecular filter traps for specific molecular weight species. It is obvious that at least one binding partner must be confined to a flow channel. In one embodiment, the ligand can be immobilized on an interior surface of the flow channel by coating the inside of the channel with a photo-activated compound followed by filling the channel with a chemically modified ligand. A laser shining through the channel wall causes the ligand to react only with the surface compounds that are exposed to a specific spectrum light energy creating a spatially defined detection gate. The channel can then be flushed, leaving the specific area of the channel derivatized with the binding ligand. The ligand may also be immobilized on a membrane or microscreen fitted across the flow channel or immobilized on a polymer on a microscreen of a membrane. The ligand can also be placed on beads that are restricted by membranes or screens, or are retained on a given section of a flow channel by the pH gradient such as an H-filter, known in the art. In this H-filter the pH changes along the path to disassociate and recover the beads for re-circulation in the same location.

The following examples are intended to illustrate the benefits of the present invention, but do not exemplify the full scope of the invention.

EXAMPLE 1

Forming SAMs on Gold Nanoparticles that Present Both Biotin and NTA

SAM protocol. 1.5 mL of Auro Dye Forte (gold colloids) were pelleted on a benchtop microfuge at 14 k for 10 minutes. The supernatant was removed and reserved. The colloid-containing pellet was resuspended in 100 uL of the reserved storage buffer which is a surfactant solution. 100 ul of a DMF solution containing 10 uM biotin-thiol, 10 uM NTA-thiol, and 580 uM of a carboxy-terminated, C11 thiol was added to the colloid solution and incubated for 2 hours, then pelleted. The supernatant was then removed and discarded. The pellet was then resuspended in 50 ul of the surfactant storage buffer. 100 uL of a 400 uM tri-ethylene glycol-terminated thiol solution was added to the resuspended colloid pellet and heat cycled in a water bath as follows: 2 minutes at 55° C.; 2 minutes at 37° C.; 1 minute at 55° C.; and 2 minutes at 37° C. The solution was returned to room temperature, then pelleted again at 14 k for 10 minutes. The supernatant was removed and the pellet was resuspended in 100 ul 10 mM phosphate buffer pH 7.4, 100 mM NaCl. 100 uL of a surfactant solution containing 1% NiSO4 was added such that the NTA metal chelate complexes the Ni(II) and the moiety is then ready to capture histidine-tagged species.

EXAMPLE 2

Forming Nanostructures Comprised of Gold Colloids Linked into a 3-Dimensional Network by Interconnecting DNA FIGS. 5A and 5B are drawings that illustrate the strategy.

As is familiar to those skilled in the art, double stranded DNA that is modified at each end with a biotin moiety can be generated by performing PCR on a DNA template using biotinylated primers. Both 1 kb and 2 kb DNA fragments were generated to allow formation of nanostructures with different pore size. The PCR products were purified on an agarose gel using standard techniques.

Figure 11:
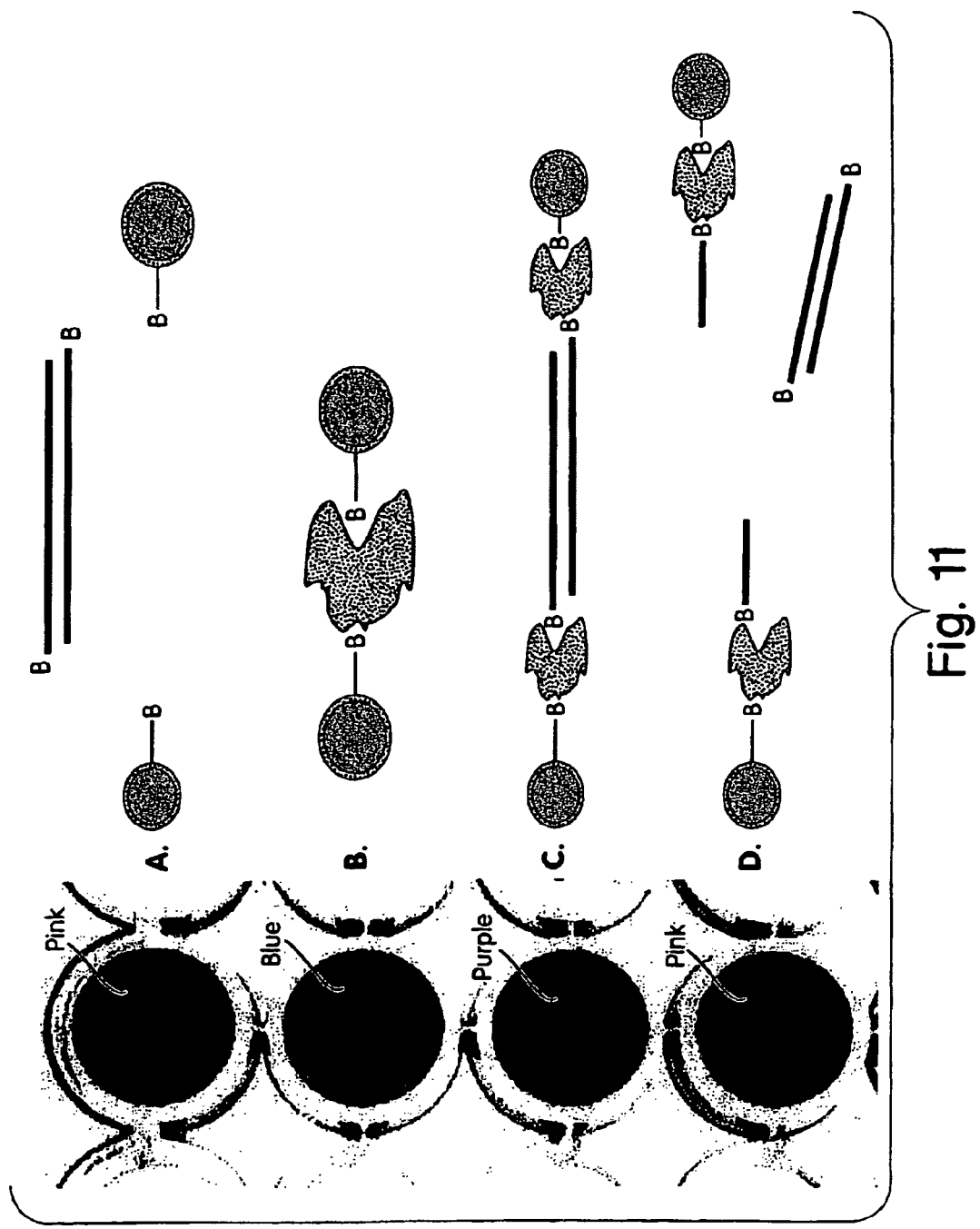
FIG. 11 is a composite of photocopies of digital photos of experimental test wells, and schematic illustrations that illustrate the corresponding experiment, showing that a colloid-DNA nanostructure is formed when biotin-SAM-coated colloids are incubated with streptavidin and biotinylated DNA.

FIG. 11 is a photocopy of a composite of digital photos and cartoons that illustrate the corresponding experiment. This figure shows that a colloid-DNA nanostructure is formed when biotin-SAM-coated colloids are incubated with streptavidin and biotinylated DNA. The formation of colloid-DNA nanostructures is detected by detecting a color change of the colloid and DNA containing solution. It is an inherent property of gold colloids that when they are dispersed in a homogeneous solution, the solution appears pink. However, if the colloids are forced close together, the solution turns from pink toward blue, with the degree of blue dependent on the distance between the colloids.

10 ul of 0.02 mg/ml streptavidin solution was incubated with either 1 kb biotinylated dsDNA (C), biotinylated dsDNA and an excess of biotinylated single-stranded DNA primers (D), or buffer in place of DNA (B), and added to 30 ul of gold colloids derivatized with SAMs that presented 2% biotin and 2% NTA-Ni(II) in a phosphate buffer in a final volume of 100 ul per well. Control well (A) contains 1 kb biotinylated DNA but no streptavidin. As seen above, biotin-colloids plus DNA in the absence of streptavidin (A) do not change color. Biotin-colloids plus streptavidin (B) change color within ten minutes from red to blue, and eventually the solution clears. Biotin-colloids plus streptavidin in the presence of biotinylated DNA change color from red to purple, indicating that the biotinylated ends of the DNA competed with the biotin on the colloids for binding of streptavidin. Over time (greater than 1 hour) a mixture of biotin-colloids and streptavidin turned completely blue and the aggregates crashed out of solution, leaving the solution in the well clear. The biotin-colloids plus streptavidin and 1 kb DNA remained the same color indefinitely, indicating that the incorporation of biotinylated DNA into the colloid-streptavidin network keeps the colloids at a distance such that the network remains suspended in solution. The contents of wells B and C were removed and pelleted and the pellets were stained with ethidium bromide. The pellet from well (C) showed DNA in the pellet, confirming that the DNA had incorporated into the network. Biotin-colloids plus streptavidin in the presence of single-stranded biotinylated primers (D) did not change color, as the biotin on the primers competed with the biotin-colloids for binding to streptavidin. Because the primers are biotinylated only at one end, they did not serve to string together a colloid-DNA-streptavidin network as the biotinylated 1 kb DNA did, and the well remained pink.

EXAMPLE 3

Reconfigurable Nanostructures

Figure 12:
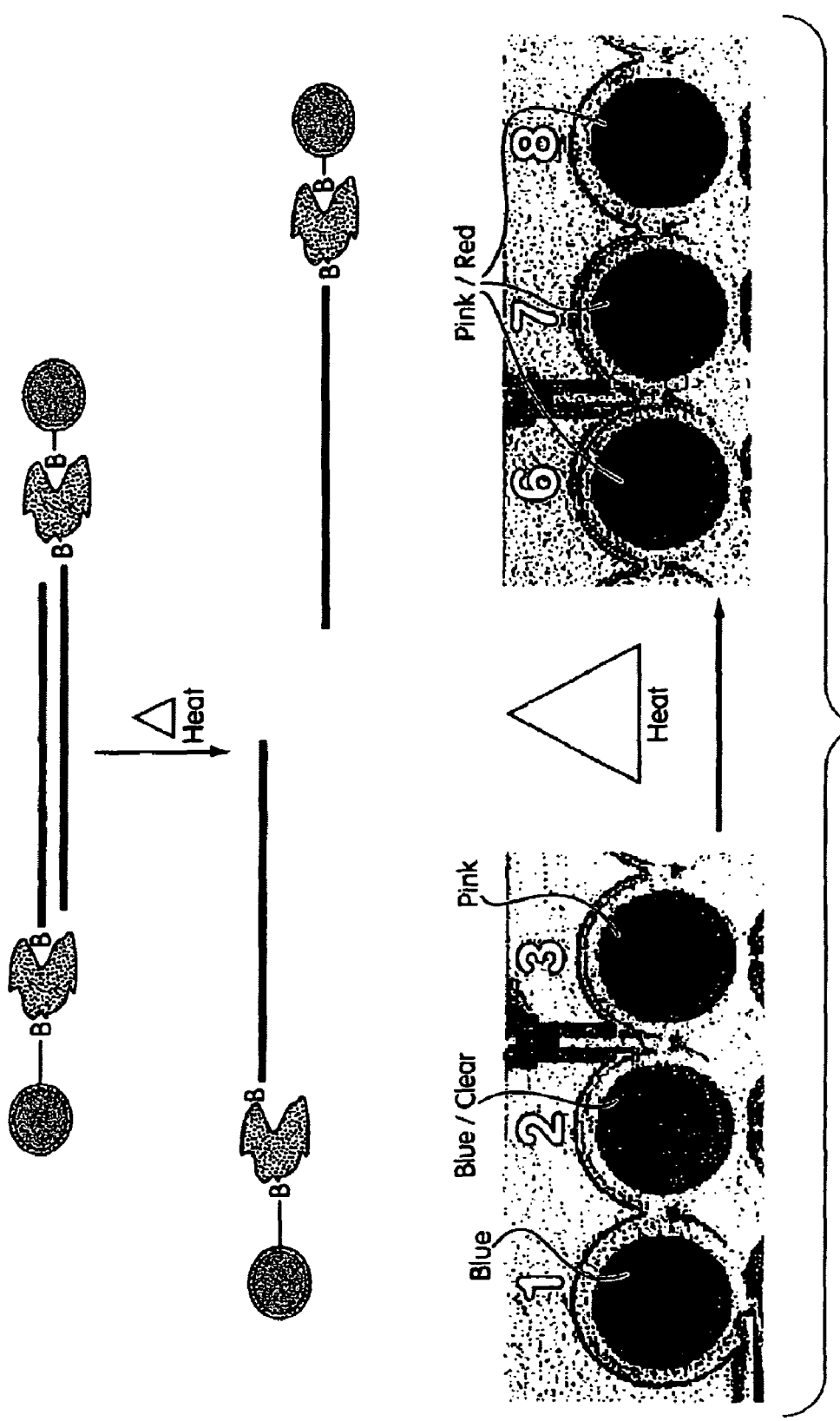
FIG. 12 presents experimental results showing that nanostructures can be reconfigured in situ by melting the dsDNA that connects the nanoparticles with the addition of heat.

Self-assembled 3-dimensional structures that are formed from the interaction of nanoparticles and dsDNA were disassembled and reconfigured in situ. The addition of heated water caused the DNA strands to melt or disassociate. Since each DNA strand was only biotinylated at one end, strand melting caused the nanostructure to disassemble. Experiments pictured in FIG. 12 showed that nanostructures were melted when the solutions were heated. These results indicate that nanoparticle-DNA structures can be configured and reconfigured in situ. The results also argue that what is forming are in fact networks rather than non-specific aggregates, which would not be prone to disassemble. Referring still to FIG. 12, on the left (1) is a photocopy of a photograph of a solution containing biotinylated dsDNA, biotin-SAM-coated gold colloids, and streptavidin; (2) is a photocopy of a photograph of a solution containing biotin-SAM-coated gold colloids, and streptavidin, but no biotinylated dsDNA; and (3) is photocopy of a photograph of a solution containing biotinylated dsDNA, biotin-SAM-coated gold colloids, but no streptavidin. The solutions were then boiled for 2 minutes. As can be seen in the corresponding wells on the right, the color of the two blue solutions reverted to pink, indicating melting of the nanostructure.

EXAMPLE 4

Figure 13:
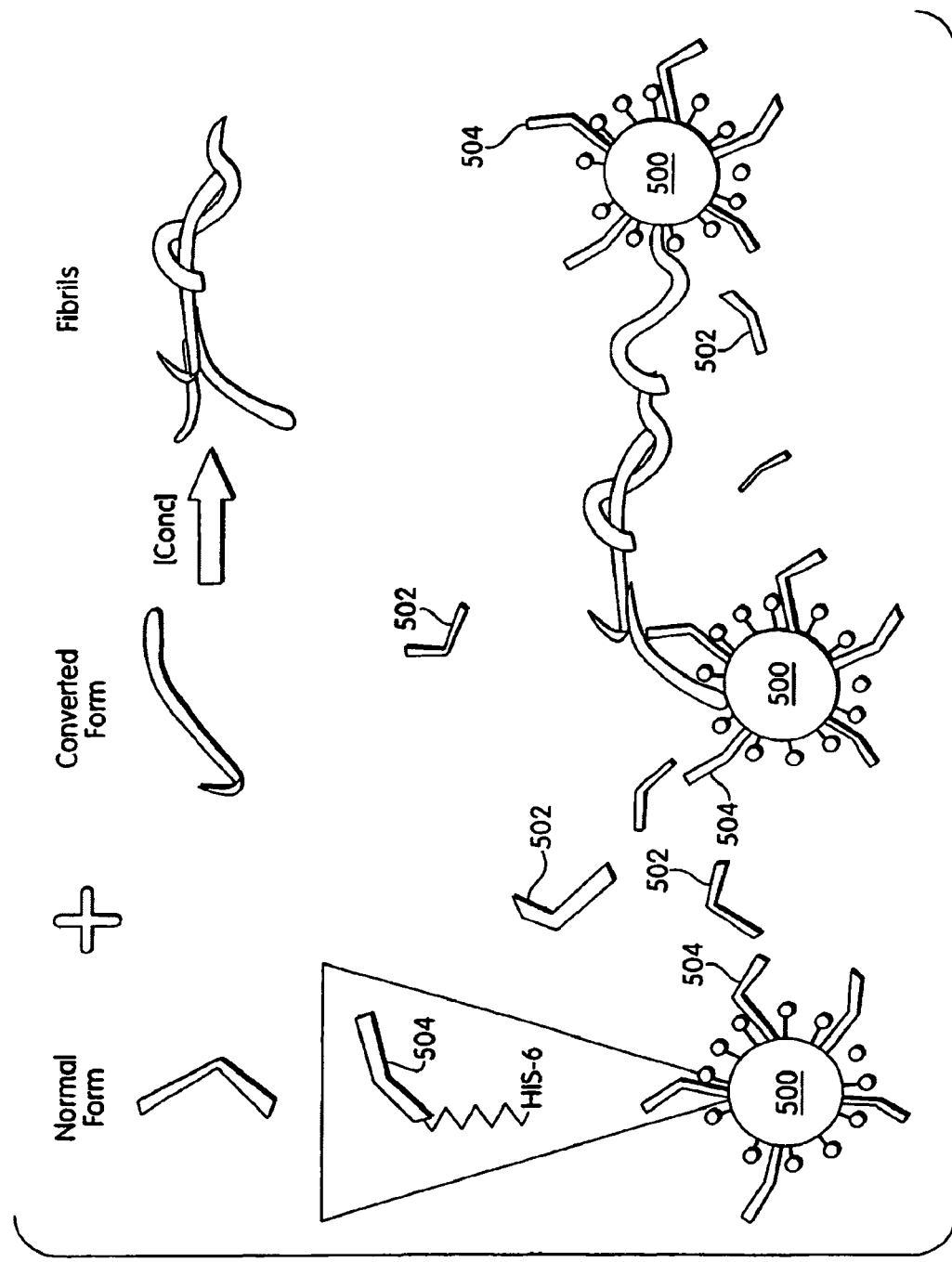
FIG. 13 is a schematic illustration demonstrating that nanostructures can also be assembled by mixing aggregation-prone species with derivatized nanoparticles.
Figure 14:
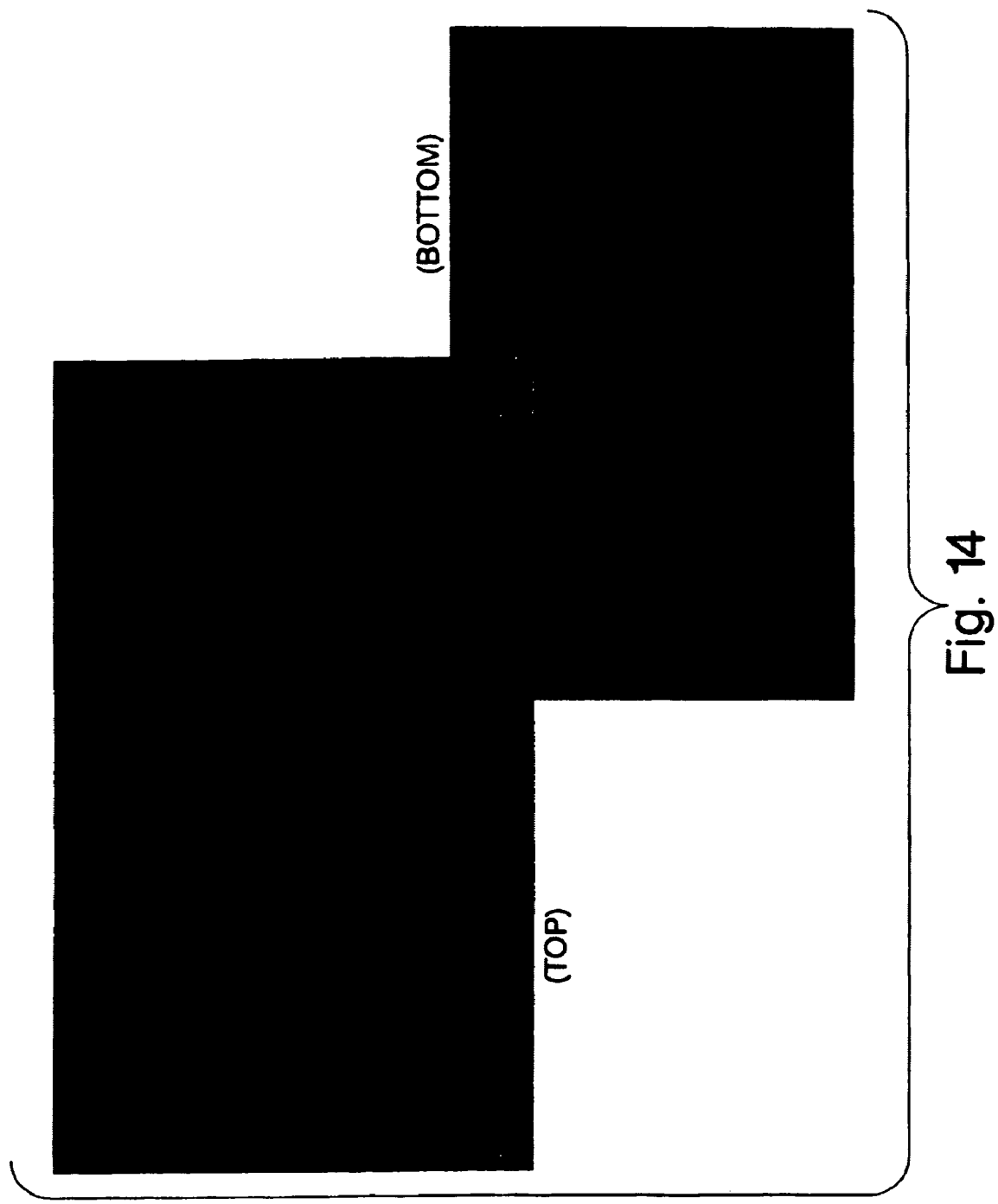
FIG. 14 is a photocopy of a photograph showing that a peptide-nanoparticle nanostructure that results from mixing histidine-tagged beta-amyloid peptides with NTA-Ni(II)-bearing nanoparticles under 40-fold magnification (top), and that a histidine-tagged random sequence peptide when mixed with NTA-Ni(II) nanoparticles does not produce nanostructures (bottom)
Figure 15:
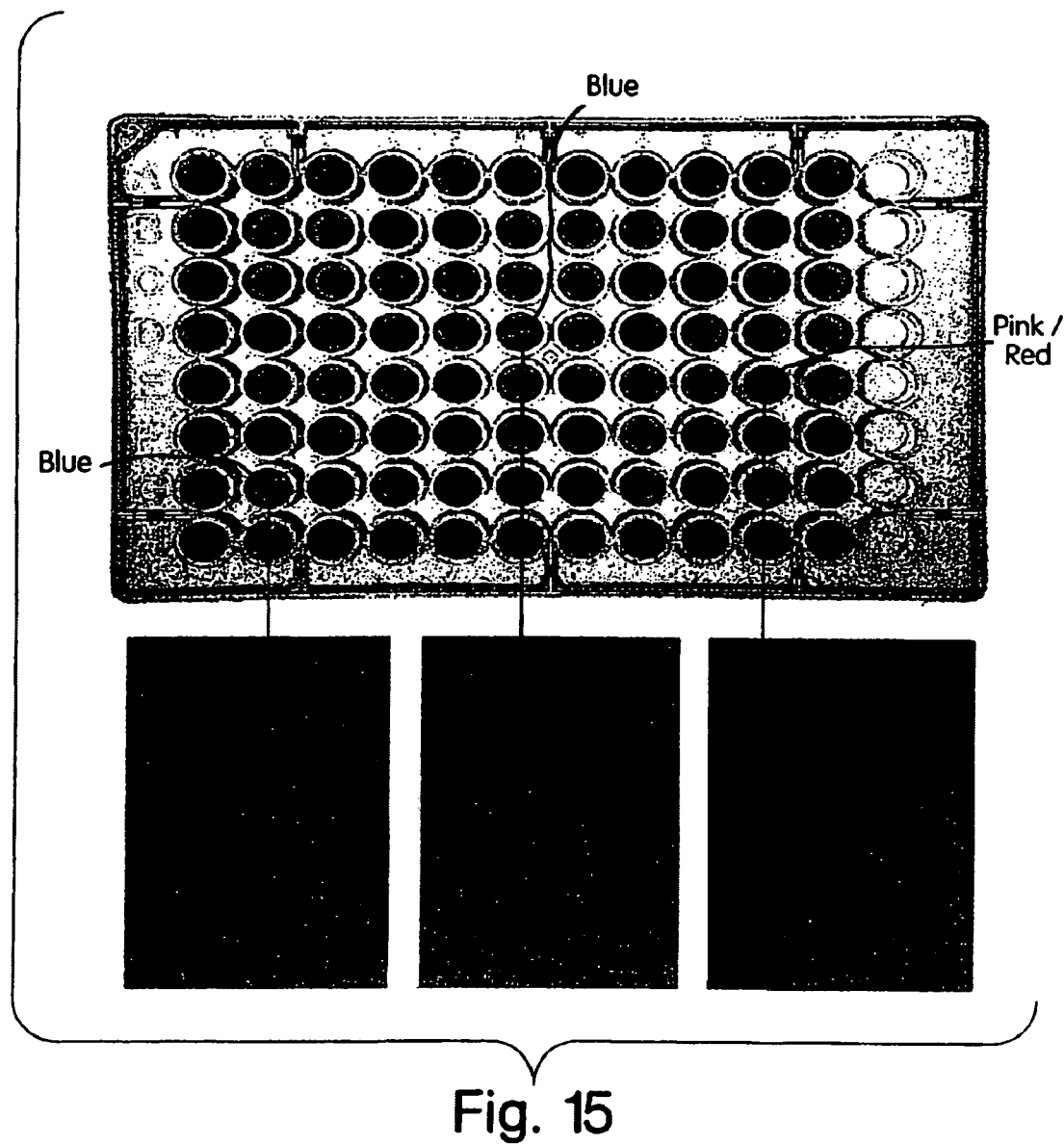
FIG. 15 is a photocopy of a digital image that shows that the degree of nanoparticle formation correlates to a color change of a colloidal gold solution.

Forming Nanostructures Comprised of Gold Colloids Linked to Peptides that Naturally Self-aggregate FIG. 13 illustrates that nanostructures can also be assembled by mixing aggregation-prone species with derivatized nanoparticles. Beta-amyloid peptides are known to self-aggregate to form fibrils and plaques, which are characteristic of Alzheimer's disease. It is also known that beta-amyloid peptides self-aggregate in vitro to form disease-like fibrils. Gold colloids 500 that were derivatized with self-assembled monolayers that presented NTA-Ni(II), to capture histidine-tagged peptides, were mixed with beta-amyloid peptides 502, some of which 504 bore histidine tags to facilitate attachment to the colloids. FIG. 14 is a photocopy of a photograph that shows that a peptide-nanoparticle nanostructure that results from mixing histidine-tagged beta-amyloid peptides with NTA-Ni(II)-bearing nanoparticles. Nanostructure formation was clearly visible under 40-fold magnification (top), while a histidine-tagged random sequence peptide when mixed with NTA-Ni(II) nanoparticles does not produce nanostructures (bottom). FIG. 15 is a photocopy of a digital image that shows that the degree of nanoparticle formation correlates to a color change of the colloidal gold solution. Due to an inherent optical property of colloidal gold, there is a color change of the colloid solution, from pink to blue, when colloidal particles are drawn into close proximity as the particle-attached beta-amyloid peptides self-aggregate and form a nanostructure. This figure shows a drug screening assay in which a different drug candidate has been added to histidine-tagged beta-amyloid peptides in each well of a 96-well plate. Controls are along the left-most column, with the upper half containing no drug and the lower half containing a histidine-tagged random sequence peptide. The contents of representative wells are shown magnified by 40-fold to illustrate that the degree of color change correlates to the degree of nanostructure formation.

EXAMPLE 5

Nanostructures Anchored to a Spatially Defined Region on a Gold-coated Surface to Form a Structure that Acts as a Nano-scale Filter, Concentrator, or Sensor Similar methods can be used to form these functional nanostructures in micro- or nano-scale flow channels.

A patterned SAM that presented a thin stripe of biotin in a background of an inert species was formed on a gold surface as follows. A pipette tip was dipped into a DMF solution containing 20% biotin-thiol and 80% tri-ethylene glycol-terminated thiol, with a total thiol concentration of 600 micromolar, and dragged across a gold-coated substrate, herein called a chip. The chips were incubated at room temperature for 30 minutes then transferred to scintillation vials containing a 1 ml solution of 400 uM tri-ethylene glycol-terminated thiol, such that the entire surface of the chip is covered. The chip-containing vials were then heat cycled in water baths as follows: 2 minutes at 55° C.; 2 minutes at 37° C.; 1 minute at 55° C.; and 2 minutes at 37° C. The chips were cooled to room temperature. Chips were rinsed in DMF then water and dried under a stream of argon. A solution containing 30 uL biotin-NTA-SAM-coated colloids, prepared as described above, 10 uL 0.02 mg/ml streptavidin solution, and 10 uL of 1 kb dsDNA that was biotinylated at both ends was incubated with the chips. After a 15 minute incubation period, the chips were rinsed in water.

Figure 16D:
FIG. 16 is a photocopy of a set of digital photos that show that nanoparticle-DNA nano-structures are formed and attached, in a spatially defined manner, to a gold-coated surface that has been derivatized to bear moieties that anchor the nano-structure.
Figure 16C:
Figure 16B:
Figure 16A:

The formation of a colloid-DNA nanostructure, attached to a thin biotin-presenting strip on a chip surface, can be readily seen as a darkened stripe (due to the red color of the gold colloids) in FIG. 16B, which shows photocopies of photographs of the chips. Areas of nanostructure formation appear darkened as the gold colloids agglomerate on the surface. Colloid-DNA networks were formed when streptavidin, which has 4 binding sites for biotin, simultaneously bound to biotin-presenting colloids and biotin-modified DNA, see FIGS. 5A and 5B. Similarly, streptavidin, free in solution, simultaneously bound to exposed biotin moieties in the nanostructure and exposed biotin moieties on the chip surface. The nanostructure appears as a darkened stripe, due to the red color of the gold colloids. Controls: FIG. 16A shows that the entire surface of the chip is uniformly colored red (darkened). A uniform biotin-SAM was formed over the entire surface of this chip, rather than in a stripe. There is no red coloration (darkened areas) on the chips shown in FIGS. 16C and 16D, indicating that the colloid-DNA nanostructure did not attach to the chip surfaces. The chips used in FIGS. 16C and 16D were coated with uniform SAMs that presented NTA (C) and tri-ethylene glycol (D) only.

Although the invention has been described with respect to various embodiments, it should be realized that this invention is also capable of a wide variety of further and other embodiments within the spirit of this invention. The nanostructures described herein can be used in a variety of detection devices. Determination of the best techniques may depend upon the specifics of the materials being detected and the chemistry and targets and flow rates, etc. Detectors that are electronic in nature are also compatible with the described nanostructures.

While several embodiments of the invention have been described and illustrated herein, those of ordinary skill in the art will readily envision a variety of other means and structures for performing the functions and/or obtaining the results or advantages described herein, and each of such variations or modifications is deemed to be within the scope of the present invention. More generally, those skilled in the art would readily appreciate that all parameters, dimensions, materials, and configurations, etc. described herein are meant to be exemplary and that actual parameters, dimensions, materials, and configurations, etc. will depend upon specific applications for which the teachings of the present invention are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described. The present invention is directed to each individual feature, system, material and/or method described herein. In addition, any combination of two or more such features, systems, materials and/or methods, provided that such features, systems, materials and/or methods are not mutually inconsistent, is included within the scope of the present invention. In the claims, all transitional phrases or phrases of inclusion, such as "comprising," "including," "carrying," "having," "containing," and the like are to be understood to be open-ended, i.e. to mean "including but not limited to." Only the transitional phrases or phrases of inclusion "consisting of" and "consisting essentially of" are to be interpreted as closed or semi-closed phrases, respectively.

What is claimed is:

1. An article comprising: a channel able to contain a flowing fluid; and a porous member comprising a network of colloid particles interconnected with molecular species, wherein the porous member comprises at least two pores at least partially spanning the channel, wherein average diametric pore size is less than 0.5 micron, wherein the porous member completely spans the channel.

2. The article as in claim 1, wherein the channel has a diametric cross-sectional dimension of less than about 500 microns.

3. The article as in claim 1, wherein the channel has a diametric cross-sectional dimension of less than about 300 microns.

4. The article as in claim 1, wherein the channel has a diametric cross-sectional dimension of less than about 100 microns.

5. The article as in claim 1, wherein the channel has a diametric cross-sectional dimension of less than about 50 microns.

6. The article as in claim 1, wherein the porous member has an average diametric pore size of less than 0.2 micron.

7. The article as in claim 1, wherein the porous member has an average diametric pore size of less than 100 nanometers.

8. The article as in claim 1, wherein the porous member has an average diametric pore size of less than 50 nanometers.

9. The article as in claim 1, wherein the porous member has an average diametric pore size of less than 10 nanometers.

10. The article as in claim 1, wherein the porous member has an average diametric pore size of less than 5 nanometers.

11. The article as in claim 1, wherein the molecular species are fastened to the colloid particles via affinity tag/recognition entity pairs.

12. The article as in claim 1, wherein at least some colloid particles are interconnected with other colloid particles via connections, each connection including, at least one point in the connection, a single molecule.

13. The article as in claim 1, wherein the network of colloid particles are interconnected via oligonucleotides.

14. The article as in claim 1, wherein the porous member has an open area of pore size in the aggregate forming at least 70% diametric cross-sectional area of channel open to flow.

15. The article as in claim 14, wherein the open area is at least 80%.

16. The article as in claim 15, where the open area is at least 90%.

17. The article as in claim 16, wherein the open area is at least 95%.

18. The article as in claim 17, wherein the open area is at least 98%.

19. The article as in claim 1, wherein the channel comprises a groove formed in a surface.

20. The article as in claim 1, wherein the channel is an elongated, enclosed structure having an inlet and an outlet.

21. The article as in claim 20, wherein the channel has a diametric cross-sectional dimension of less than 500 microns and the porous member completely spans the channel and comprises a network of colloid particles interconnected with molecular species and has an open area of pore size in the aggregate forming at least 70% diametric cross-sectional area of the channel open to flow.

22. The article as in claim 21, wherein the porous member has the open area of at least 95% an open area of pore size in the aggregate forms at least 95% diametric cross-sectional area of the channel open to flow and an average diametric pore size of is less than 10 nanometers.

23. The article as in claim 1, wherein the molecular species comprises an oligonucleotide.

24. The article as in claim 1, wherein the molecular species comprises a polymer.

25. The article as in claim 24, wherein the polymer is a synthetic polymer.

26. The article according to claim 1, wherein the article further comprises a means for detecting flow rate.

27. The article according to claim 26, wherein the means for detecting flow rate comprises means for detecting flow drop.

28. The article according to claim 27, wherein the means for detecting flow drop is a differential pressure monitor.

29. The article according to claim 1, wherein the colloidal particle is coated with self assembled monolayer (SAM) or self assembled mixed monolayer.

30. The article according to claim 1, wherein the interconnection can be dissociated by disrupting biological interactions that connect them to the channel.

31. A method comprising: passing a fluid through the article according to claim 1; allowing a chemical, biological, or biochemical agent within the fluid to bind to a binding partner of the agent immobilized relative to the porous member; determining the binding.

32. A method as in claim 31, comprising determining the binding by determining a pressure differential change across the porous member.

33. A method as in claim 31, comprising determining the binding qualitatively.

34. A method as in claim 31, comprising determining the binding quantitatively.

35. A method as in claim 31, wherein the porous member comprises a network of colloid particles interconnected with molecular species spanning a channel through which the fluid is passed.

36. A method as in claim 35, wherein the channel is an elongated, enclosed channel having an inlet and an outlet, and the porous member completely spans the channel such that a fluid flowing through the channel must pass through the porous member.

37. A method as in claim 36, wherein the porous member comprises a network of colloid particles interconnected with molecular species.

38. A method as in claim 37, wherein the molecular species comprise oligonucleotides.

39. A method as in claim 37, wherein the molecular species comprise polymers.

40. A method as in claim 39, wherein the polymer is comprised of synthetic polymers.

41. A method as in claim 37, wherein the porous member comprises a network including colloid particles at least some of which are connected to other colloid particles by a connection including a single molecule.

42. A method as in claim 31, wherein the fluid is an analysis flow of fluid diverted from a main flow of fluid, the method further comprising controlling the main flow of fluid in response to the determining step.

43. A method as in claim 42, wherein the agent is an agent desirably excluded from the main flow of fluid, the method comprising reducing the main flow of fluid in response to the determining step.

44. A method as in claim 43, wherein the fluid is water.

45. A method comprising in the article of claim 1: replacing a first binding partner of a chemical, biological, or biochemical agent immobilized relative to a porous member with a second binding partner without disassembling the porous member relative to the channel.

46. A method comprising in the article of claim 1: passing a fluid through a porous medium; allowing a chemical, biological, or biochemical agent within the fluid to bind to a binding partner of the agent immobilized relative to the porous member; and causing the chemical, biological, or biochemical agent to release from the porous member.

47. A method as in claim 46, further comprising determining the chemical, biological, or biochemical agent downstream from the porous member.

48. A method as in claim 46, comprising concentrating the agent at the porous member during a first period of time, and during a second period of time shorter than the first period of time, releasing agent concentrated at the porous member and determining the agent.

49. A method as in claim 46, comprising allowing the agent to bind to the binding partner to an extent necessary to essentially block flow of fluid through the porous member, then causing the agent to release from the porous member thereby allowing fluid to flow through the porous member.

50. A method as in claim 49, comprising chemically causing the agent to release from the porous member.

51. A method as in claim 49, comprising thermally causing the agent to release from the porous member.

52. A method comprising in the article of claim 1: allowing a first chemical, biological, or biochemical agent to become immobilized relative to a first colloid particle and allowing a second chemical, biological, or biochemical agent to become immobilized relative to a second colloid particle; based at least in part on the identity of the first and second agents, directing the first colloid particle to a first fluid channel and directing the second colloid particle to a second channel.

53. A method comprising in the article of claim 1: allowing a chemical, biological, or biochemical agent to become immobilized relative to a colloid particle; determining at least one characteristic of the agent; based at least in part on the characteristic, directing the colloid particle to a first fluid channel rather than a second fluid channel, each channel capable of receiving the colloid particle prior to the directing step.

54. A method as in claim 53, comprising allowing multiple agents to become immobilized relative to multiple colloid particles, the agents being different from each other, determining at least one characteristic of at least one agent at a first location, then moving at least some of the colloid particles to a second location and determining at least one characteristic of at least one, different agent at the second location.

55. A method comprising in the article of claim 1: allowing a chemical, biological, or biochemical agent to become immobilized relative to a colloid particle; determining at least one characteristic of the agent at a first detection location; and determining at least one characteristic of the agent at a second detection location.

56. A method as in claim 55, comprising determining a first characteristic of the agent at the first location along a fluid flow path, moving a fluid containing the colloid particle along the flow path to the second detection location and determining a second characteristic of the agent at the second location.

57. A method comprising in the article of claim 1: determining the identity of a chemical, biological, or biochemical agent by determining the flow path of a fluid, initially containing the agent, where the fluid has a plurality of flow path options.

58. A method as in claim 57, comprising allowing the agent to bind to a binding partner along the flow path thereby altering the flow path of the fluid.

* * * * *